US010492669B2

(12) United States Patent
Aoki et al.

(10) Patent No.: US 10,492,669 B2
(45) Date of Patent: Dec. 3, 2019

(54) BENDING DEVICE, CONTROL DEVICE, AND MEDICAL INSTRUMENT

(71) Applicants: Sharp Kabushiki Kaisha, Sakai, Osaka (JP); Public University Corporation Hiroshima City University, Hiroshima-shi, Hiroshima (JP)

(72) Inventors: Hitoshi Aoki, Sakai (JP); Kazunori Morita, Sakai (JP); Toshihisa Gotoh, Sakai (JP); Kazuhiro Taniguchi, Hiroshima (JP); Masazumi Okajima, Hiroshima (JP); Satoshi Iwaki, Hiroshima (JP)

(73) Assignees: SHARP KABUSHIKI KAISHA, Sakai (JP); PUBLIC UNIVERSITY CORPORATION HIROSHIMA CITY UNIVERSITY, Hiroshima (JP)

( * ) Notice: Subject to any disclaimer, the term of this patent is extended or adjusted under 35 U.S.C. 154(b) by 274 days.

(21) Appl. No.: 15/314,154

(22) PCT Filed: Feb. 19, 2015

(86) PCT No.: PCT/JP2015/054588
§ 371 (c)(1),
(2) Date: Nov. 28, 2016

(87) PCT Pub. No.: WO2015/182178
PCT Pub. Date: Dec. 3, 2015

(65) Prior Publication Data

US 2017/0196436 A1 Jul. 13, 2017

(30) Foreign Application Priority Data

May 30, 2014 (JP) ................................ 2014-113355

(51) Int. Cl.
*A61B 1/005* (2006.01)
*A61B 1/018* (2006.01)
(Continued)

(52) U.S. Cl.
CPC ........ *A61B 1/0057* (2013.01); *A61B 1/00078* (2013.01); *A61B 1/018* (2013.01);
(Continued)

(58) Field of Classification Search
CPC ...... A61B 1/0071; A61B 1/0051–0053; A61B 1/015
(Continued)

(56) References Cited

U.S. PATENT DOCUMENTS 4,575,185 A * 3/1986 Wentzell ............... F22B 37/002 138/121
4,832,473 A * 5/1989 Ueda ................... A61B 1/0053 359/367
(Continued)

FOREIGN PATENT DOCUMENTS

JP 04-82527 A 3/1992
JP 06-125868 A 5/1994
(Continued)

*Primary Examiner* — Matthew J Kasztejna
(74) *Attorney, Agent, or Firm* — Keating & Bennett, LLP

(57) ABSTRACT

The present invention provides a bending device which is capable of easily controlling a bending motion with superior controllability. A portion of an elastic tube body (11) opposite a portion in which a non-stretching body (4) is fixed inflates in a circumferential direction of the elastic tube body (11) in response to increase in an internal pressure of the elastic tube body (11), and an elastic tube (1P) bends in a step-wise angle corresponding to the number of layers of a multi-layer structure. The portion of the elastic tube body (11) in which the non-stretching body (4) is fixed is thicker than the remaining portion of the elastic tube body (11).

17 Claims, 25 Drawing Sheets

1a, 1b, 1c, 1d, 1k, 1m, 1n, 1P: ELASTIC TUBES
4: NON-STRETCHING BODY
11: ELASTIC TUBE BODY
13: FIXING PORTION
31: BENDING PORTION

(51) Int. Cl.

| | |
|---|---|
| ***A61B 5/04*** | (2006.01) |
| ***A61B 1/00*** | (2006.01) |
| ***A61M 25/01*** | (2006.01) |
| *A61B 18/14* | (2006.01) |
| *A61B 18/00* | (2006.01) |

(52) U.S. Cl.

CPC ........... *A61B 5/04* (2013.01); *A61M 25/0155* (2013.01); *A61B 18/1492* (2013.01); *A61B 2018/00982* (2013.01)

(58) Field of Classification Search

USPC ........ 600/115–116, 121–125, 140, 143, 146, 600/152

See application file for complete search history.

(56) References Cited

U.S. PATENT DOCUMENTS

| | | | | |
|---|---|---|---|---|
| 4,890,602 | A * | 1/1990 | Hake | A61B 1/0053 600/144 |
| 4,962,751 | A * | 10/1990 | Krauter | A61B 1/0053 600/152 |
| 5,018,436 | A * | 5/1991 | Evangelista | F01B 19/00 600/152 |
| 5,018,506 | A * | 5/1991 | Danna | A61B 1/0053 600/152 |
| 5,083,498 | A * | 1/1992 | Sato | F15B 15/125 73/731 |
| 5,179,934 | A * | 1/1993 | Nagayoshi | A61B 1/00183 600/152 |
| 5,577,992 | A * | 11/1996 | Chiba | A61B 1/0056 600/116 |
| 6,048,307 | A * | 4/2000 | Grundl | A61B 1/0053 600/146 |
| 6,261,260 | B1 * | 7/2001 | Maki | A61L 29/04 428/35.5 |
| 6,478,772 | B2 * | 11/2002 | Maki | A61L 29/04 604/103.07 |
| 6,503,194 | B2 * | 1/2003 | Pauker | A61B 1/0055 600/146 |
| 6,875,170 | B2 * | 4/2005 | Francois | A61B 1/0053 600/141 |
| 6,899,674 | B2 * | 5/2005 | Viebach | A61B 1/0008 600/115 |
| 7,762,948 | B2 * | 7/2010 | Hirata | A61B 1/0051 600/139 |
| 9,186,049 | B2 * | 11/2015 | Lee | G02B 23/2476 |
| 2004/0097788 | A1 * | 5/2004 | Mourlas | A61B 1/00082 600/116 |
| 2016/0249900 | A1 * | 9/2016 | Aoki | A61M 25/0155 606/130 |
| 2017/0196436 | A1 * | 7/2017 | Aoki | A61B 1/0057 |

FOREIGN PATENT DOCUMENTS

| | | | |
|---|---|---|---|
| JP | 2000-271076 | A | 10/2000 |
| JP | 2003-301807 | A | 10/2003 |
| JP | 2007-061547 | A | 3/2007 |
| JP | 2008-019984 | A | 1/2008 |
| JP | 2014-076348 | A | 5/2014 |
| WO | 2015/060034 | A1 | 4/2015 |
| WO | 2015/156022 | A1 | 10/2015 |

* cited by examiner

2: ENDOSCOPE CAMERA
5: CONNECTING TUBE
10: ENDOSCOPE PART
20: CONTROL DEVICE
21: PISTON
22: SYRINGE
23: AIR PRESSURE SENSOR
24: PISTON DRIVING UNIT
25: MICROPHONE
26: PRESSURIZATION CONTROL UNIT
28: PRESSURIZING VALVE DRIVING UNIT
30: ARTICULATED BENDING PORTION
31: BENDING PORTION
32: NON-BENDING PORTION
36: PRESSURIZING VALVE
100: ENDOSCOPE DEVICE 3a, 3b, 3c, 3d: NON-INFLATING TUBES
4: NON-STRETCHING BODY
11: ELASTIC TUBE BODY
13: FIXING PORTION
32: NON-BENDING PORTION
33: RIGID TUBE
34: NON-INFLATING BODY 1a, 1b, 1c, 1d, 1k: ELASTIC TUBES
4: NON-STRETCHING BODY
11: ELASTIC TUBE BODY
13: FIXING PORTION
31: BENDING PORTION 1a, 1b, 1c, 1d, 1k, 1m, 1n: ELASTIC TUBES
4: NON-STRETCHING BODY
11: ELASTIC TUBE BODY
13: FIXING PORTION
31: BENDING PORTION (a)
(b)
(c)
(d)
(e)
(f)
30
31d
32
31e
31f
31g
31h
34
A
B
C
D
E
F
G
H
J
30: ARTICULATED BENDING PORTION
31d, 31e, 31f, 31g, 31h: BENDING PORTIONS
32: NON-BENDING PORTION
34: NON-INFLATING BODY

TUBE E
TUBE A
TUBE J
TUBE C
TUBE G
PERIPHERAL TUBE
1j, 1k: ELASTIC TUBES
3j: NON-INFLATING TUBE
4: NON-STRETCHING BODY
30: ARTICULATED BENDING PORTION
31b, 31c, 31d: BENDING PORTIONS
32: NON-BENDING PORTION
34: NON-INFLATING BODY

BENDING DEVICE, CONTROL DEVICE, AND MEDICAL INSTRUMENT

TECHNICAL FIELD

The present invention relates to a bending device, a control device, and a medical instrument. More particularly, the present invention relates to a medical instrument as an endoscope device for taking images of an affected area during a medical procedure or an operation on a patient, for example, an endoscope device suited for use in an endoscopic surgery using a rigid endoscope such as a laparoscope or a thoracoscope, in particular a single-port laparoscopic surgery. The present invention also relates to a medical instrument equipped with a catheter, a laser scalpel, or an electric scalpel, for example, as a medical device.

BACKGROUND ART

An endoscopic surgery using a rigid endoscope such as a laparoscope or a thoracoscope is a low-invasive operation for performing a test or treatment procedure without opening the patient's abdomen. In an endoscopic surgery, a medical device such as forceps and an endoscope are separately introduced into a body cavity of the patient. The operator then sets the distal end portion of the medical device inserted into the body cavity such that it is imaged in the observation field of view of the endoscope and conducts the procedure tasks while observing the state of the area being treated with the medical device through the endoscope. In an endoscopic surgery, medical devices and an endoscope are introduced into a body cavity through four or five pipes (tubular members, so-called trocars) inserted into the body wall (for example, abdominal wall) such as in the patient's abdomen.

When cutting open or suturing an organ, the operator inserts the endoscope and medical devices into separate trocars. Trocars are disposed in advance at positions suited for the operation to be performed, and for reducing the patient's burden, they are never changed to different positions once they are set. Thus, the manipulation of the endoscope and medical devices is limited by the positions of trocars and such devices can interfere with each other depending on the circumstance of the operation.

A single-port laparoscopic surgery is a method in which a single small hole of about 15 mm is made in the patient's navel through which forceps (a medical device) and an endoscope camera are inserted for resecting and removing the gallbladder, for example. In a single-port laparoscopic surgery, a surgeon (a camera assistant) manipulates the endoscope camera to capture the image of the inside of the patient's body, which is displayed on a camera monitor outside the body. A surgeon (the operator) different from the camera assistant conducts the operation while watching the camera monitor by manipulating two pairs of forceps respectively held in his right and left hands. The endoscope camera captures the affected area of the patient from above the forceps.

Because a single-port laparoscopic surgery leaves a scar only in the navel, it adds to the advantages of endoscopic surgeries over open procedures as follows:

(1) Being cosmetically favorable due to a less noticeable scar.

(2) Less pain after the operation.

(3) Shorter hospital stay (two or three days) than conventional operation methods because of quick recovery, thus helping reducing health care costs.

(4) Capable of being safely performed on physically weak patients (elderly people) because of low burden on the body.

On the other hand, the conventional single-port laparoscopic surgeries have the following problems:

(1) Contact and interference between persons and surgery devices outside the patient's body.

(2) Contact between the operator and the camera assistant.

(3) Contact between forceps and the endoscope camera.

In order to overcome these problems of endoscopic and single-port laparoscopic surgeries, the distal end portion of an endoscope device is required to have a curvable structure for taking images of the area being treated in the abdominal cavity. Such a curving structure is typically formed from wires for manipulating multiple joints by pulling them. Another type of known curving structure produces a bending motion by supplying fluid to its interior and inflating an elastic pressurizing chamber with the pressure of the fluid (PTLs 1 and 2).

PTL 1 discloses a configuration of a flexible tube having a curving portion including three elastic pressurizing chambers per joint, where the pressurizing chambers and multiple pressurizing tubes as many as the number of pressurizing chambers are disposed on the outer periphery of the flexible tube. PTL 1 discloses embodiments with mesh tubes used as pressurizing tubes for prevention of stretching or fibrous material wrapped around the pressurizing tubes.

PTL 2, for example, discloses a configuration of a flexible tube having a curving portion with three elastic pressurizing chambers per joint, where the pressurizing chambers and multiple non-stretching pressurizing tubes as many as the number of pressurizing chambers are disposed in the wall of the flexible tube.

CITATION LIST

Patent Literature

PTL 1: Japanese Unexamined Patent Application Publication No. 6-125868 (published on May 10, 1994)

PTL 2: Japanese Unexamined Patent Application Publication No. 2000-271076 (published on Oct. 3, 2000)

SUMMARY OF INVENTION

Technical Problem

While the flexible tube of PTL 1 and the endoscope device of PTL 2 cause curving of the curving portion by pressurizing and inflating pressurizing tubes, the curving angle of the curving portion is small relative to the amount of inflation of the pressurizing tubes because the pressurizing tubes inflate uniformly in the entire circumferential direction. Thus, a large pressure needs to be applied to the pressurizing tubes so that the flexible tube curves at a desired angle, making curving not easy to control.

The configuration disclosed in PTL 1 requires at least three pressurizing tubes per joint, and the number of pressurizing tubes increases proportionately to increase of the joints. Thus, when there are many joints, it is difficult to dispose the pressurizing tubes on the outer periphery of the flexible tube, making it difficult to increase the joints over a certain number. A further problem of this configuration is that increase in pressurizing tubes that are not pressurized and pressurizing tubes that are pressurized and stiffened in a linear shape place burden on bending motions, and normal bending motions cannot be effected because pressurizing tubes that are stiffened in a case where the number of joints is large are at a higher ratio to pressurizing tubes that are stiffened in a case where the number of joints is small.

The configuration disclosed in PTL 2 requires at least three pressurizing chambers and pressurizing tubes for feeding to joints on the distal end side per joint; the pressurizing chambers and pressurizing tubes increase proportionately to increase in the number of joints, and thus they are difficult to dispose in the wall of the flexible tube when there are many joints. Also, an increased number of non-stretching pressurizing tubes as components place burden on bending motions, causing the problems of interfering with bending motions or preventing a bend from occurring.

The present invention has been made in view of these challenges and an object thereof is to provide a bending device with which bending motions can be controlled with ease and good controllability.

Furthermore, the present invention solves the aforementioned problems encountered in conventional endoscopic or single-port laparoscopic surgeries, for example, by providing a safe device capable of conducting complicated and free bending motions with good controllability despite a simple structure by employing a novel structure that uses elastic tubes for curving motions at the distal end portion of a medical instrument such as an endoscope device, and also enabling automatic manipulation of curving motions through a control device.

Solution to Problem

In order to solve the aforementioned problems, a bending device according to an aspect of the present invention includes: a tubular member having a hollow structure; and a plurality of elastic tubes disposed inside the tubular member, in which the elastic tubes each include an elastic tube body which is sealed at a distal end portion thereof and has an elongated hollow cylindrical shape, and a non-stretching body for suppressing inflation of the elastic tube body, the non-stretching body is fixed to the elastic tube body, a portion of the elastic tube body in which the non-stretching body is fixed is thicker than a remaining portion of the elastic tube body, the tubular member has a multi-layer structure on a shape of a cross section orthogonal to an axis direction of the tubular member, and a portion of the elastic tube body opposite the portion in which the non-stretching body is fixed inflates in a circumferential direction of the elastic tube body in response to increase in an internal pressure of the elastic tube body and the tubular member bends in a step-wise angle corresponding to a number of layers of the multi-layer structure.

Advantageous Effects of Invention

According to one aspect, the present invention can provide a bending device with which bending motions can be controlled with ease and good controllability.

The present invention employs a structure in which fluid (for example, air) is contained in soft elastic tubes and the elastic tubes are made to curve utilizing the pressure of the fluid. Thus, even if the articulated bending device formed from such elastic tubes contacts the treated area (for example, an organ), the individual elastic tubes deform to absorb the shock associated with the contact, causing no damage to the treated area to ensure safety. Additionally, due to the simple structure of the individual elastic tubes, they can be inexpensively manufactured and easily disposed of after use (that is, are disposable), thus facilitating maintenance of cleanliness.

Also, because it uses air pressure, for example, as the force for curving tubes, it offers the advantage of not contaminating the treated area even if air leaks from an elastic tube. Moreover, because it uses non-inflated elastic tubes as narrow tubes for insertion into the treated area (the body) during a medical procedure, the distal end portion of a medical instrument (for example, an endoscope) can be made thin. Further, since the distal end portion of the medical instrument can be automatically manipulated, there is no need for a surgeon (a camera assistant) to manipulate the distal end portion of the medical instrument and thus manipulation by such a surgeon would not interfere with the medical procedure (operation) conducted by a surgeon (the operator).

As shown above, the present invention is highly convenient for medical settings as it employs a simple structure which is easy and inexpensive to manufacture yet is disposable and non-invasive to the human body, being expected to gain wide use in medical settings.

BRIEF DESCRIPTION OF DRAWINGS

FIGS. 10(*a*) and 10(*b*) are graphs for a case of a single elastic tube alone, and FIGS. 10(*c*) and 10(*d*) are graphs for a case with another elastic tube on its outer periphery.

FIG. 11(*a*) is a state in which tube A is pressurized but not inflated yet, FIG. 11(*b*) is a state in which tube A inflates and its pressure starts to be applied to the outer peripheral tube, FIG. 11(*c*) is a state in which the outer peripheral tube also starts inflating, and FIG. 11(*d*) is a state in which the inflation of the outer peripheral tube has advanced.

FIG. 14(*a*) is a graph showing the case of the bending portion shown in Embodiment 2 for comparison, and FIG. 14(*b*) is a graph showing the case where the bending portion of Embodiment 3 is used.

DESCRIPTION OF EMBODIMENTS

Embodiment 1

Embodiments of the present invention will be described below in detail based on FIGS. 1 to 6, 10, and 11.

The bending device according to the present invention is a medical instrument to which a medical device can be attached at the distal end. While an articulated bending portion 30 having multiple deformable bending portions 31 (joints) will be described as an example of the bending device according to the present invention, the bending device according to the present invention includes a bending device with a single joint as well.

(Overview of the Medical Instrument)

Figure 1:
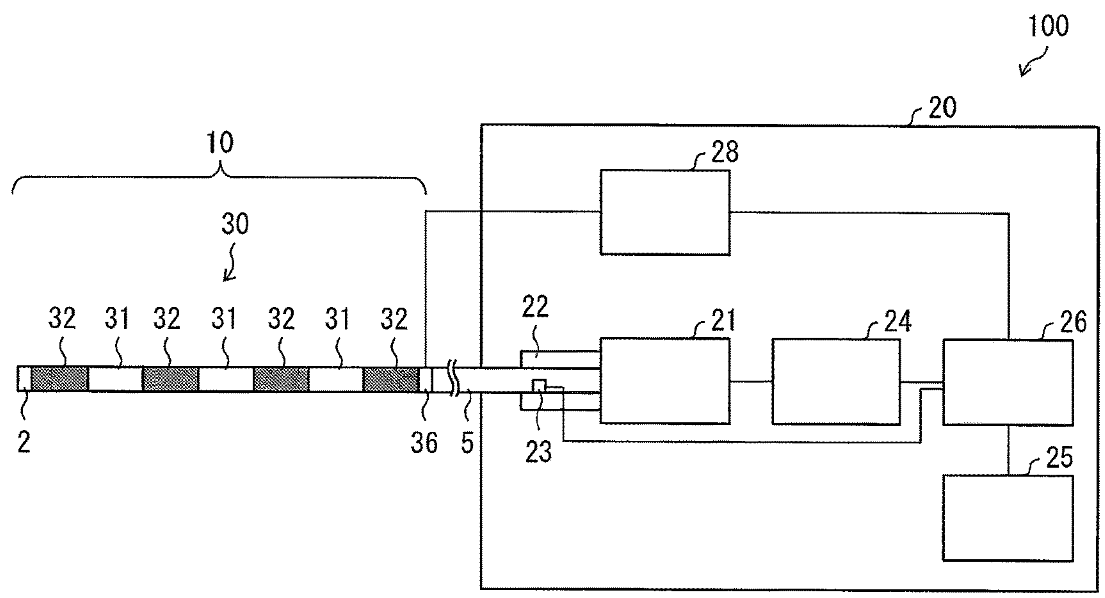
FIG. 1 shows the configuration of a medical instrument (an endoscope device) including the articulated bending portion according to Embodiment 1 of the present invention.

FIG. 1 shows the configuration of an endoscope device as an example of a medical instrument including elastic tubes according to an embodiment of the present invention. In FIG. 1, an endoscope device 100 (a medical instrument) includes an endoscope part (medical instrument part) 10 and a control device 20. The control device 20 drives and controls the endoscope part 10. The control device 20 will be described in detail later.

Figure 2:
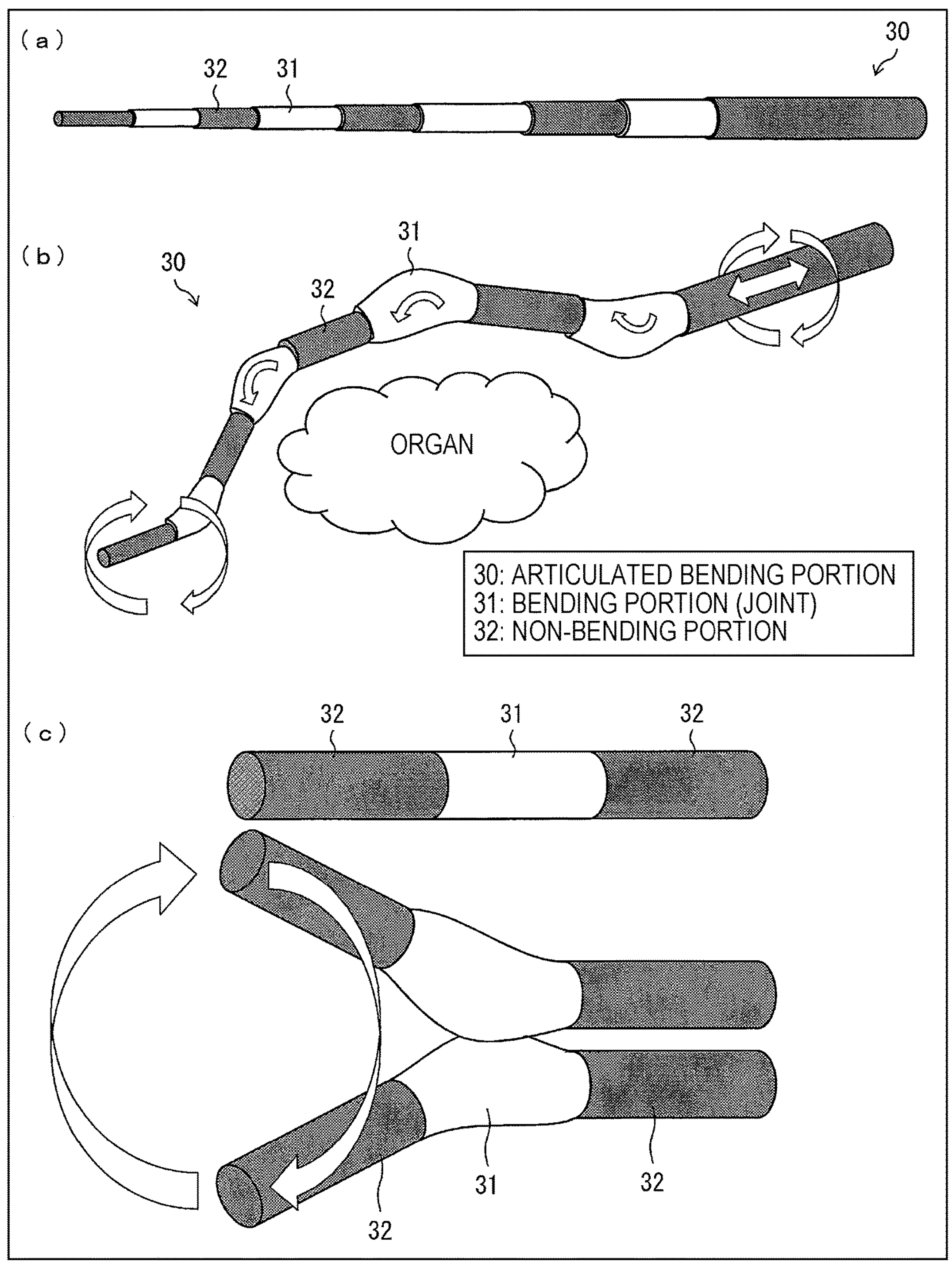
FIGS. 2(*a*) to 2(*c*) are perspective views generally showing the articulated bending portion in Embodiment 1.
Figure 3:
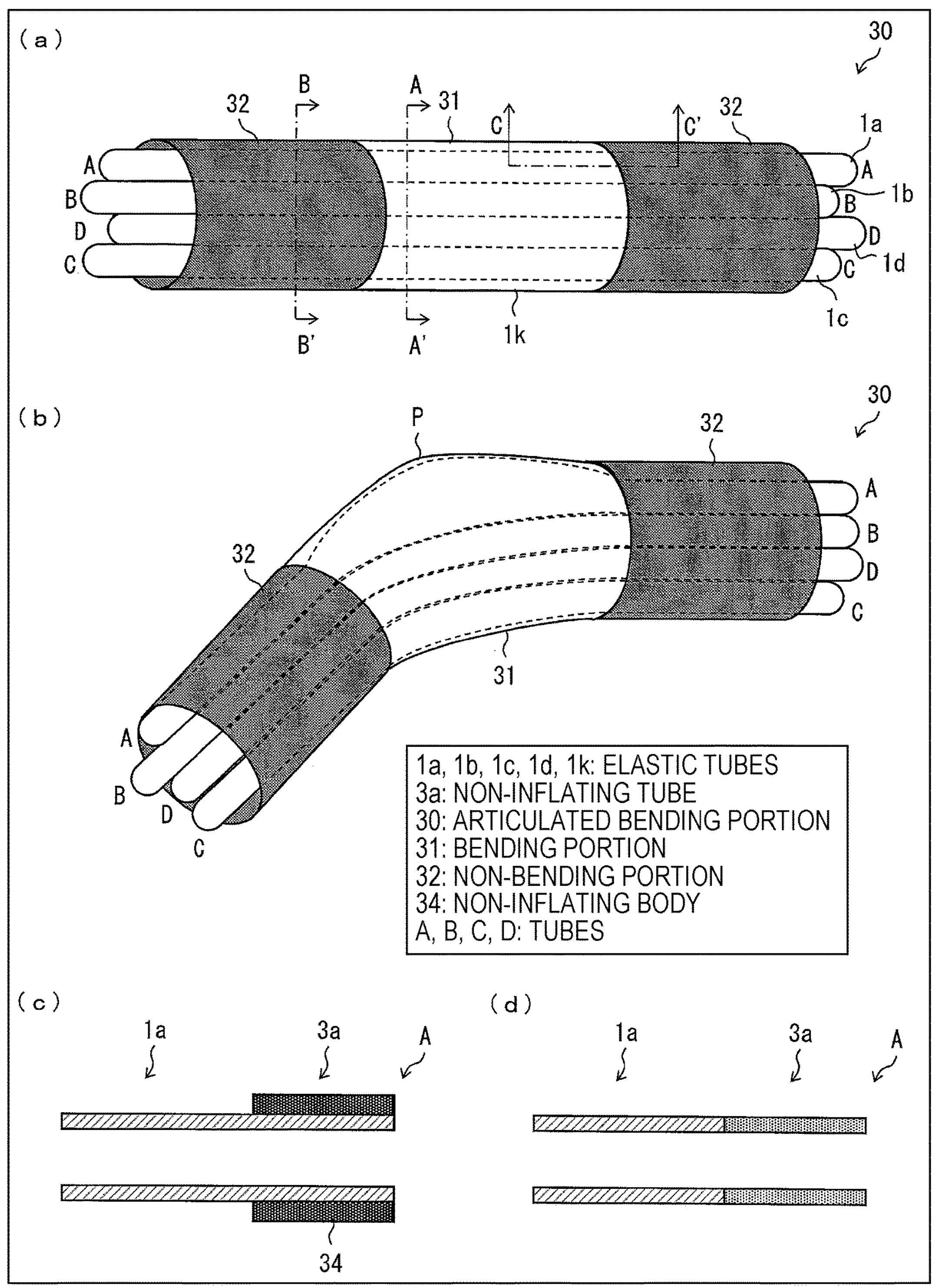
FIG. 3 shows an example of the internal structure of the articulated bending portion in Embodiment 1, FIGS. 3(*a*) and 3(*b*) being perspective views, and FIGS. 3(*c*) and 3(*d*) being cross-sectional views.

As shown in FIGS. 2 and 3, the endoscope part 10 is composed of an articulated bending portion 30 consisting of multiple bending portions (joints) 31 formed from multiple inflatable elastic tubes 1, which have an elongated, hollow cylindrical shape and contain air (gas) W, and multiple non-bending portions 32, an endoscope camera (a medical device) 2 mounted at the distal end of the articulated bending portion 30, a and non-inflating tube (not illustrated) which is provided so as to connect the articulated bending portion 30 with the pressurizing valve 36.

Figure 4:
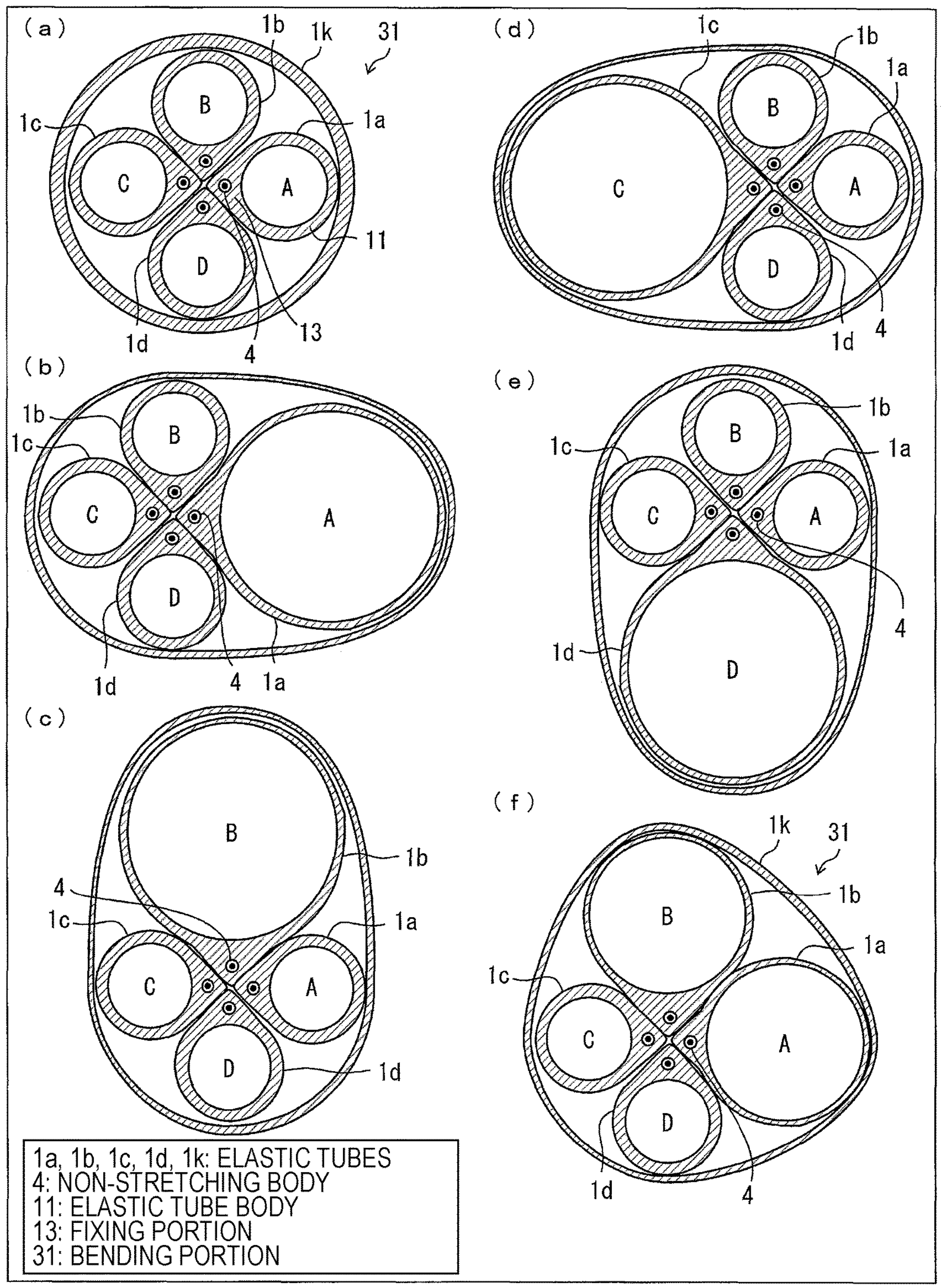
FIGS. 4(*a*) to 4(*f*) are cross-sectional views showing an example of the internal structure of a bending portion of the articulated bending portion.
Figure 5:
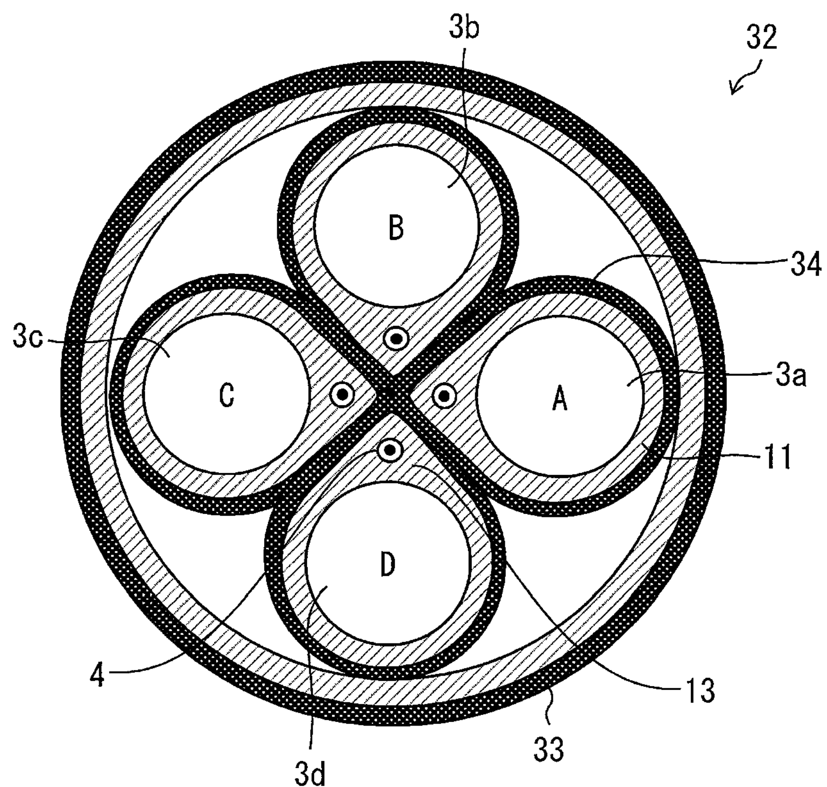
FIG. 5 is a cross-sectional view showing an example of the internal structure of a non-bending portion of the articulated bending portion.

FIG. 4(*a*) is a cross-sectional view seen from the arrow in line A-A' in FIG. 3(*a*). FIG. 5 is a cross-sectional view seen from the arrow in line B-B' in FIG. 3(*a*).

As illustrated in FIGS. 3 and 4(*a*) for example, the bending portion 31 is composed of four elastic tubes 1*a*, 1*b*, 1*c*, 1*d*, in each of which a flexible non-stretching body 4 fixed in the long-axis direction is embedded, and an elastic tube 1*k* (a tubular member) that has a hollow structure and accommodates the elastic tubes 1*a* to 1*d* inside.

The non-bending portion 32 is composed of four non-inflating tubes 3*a* to 3*d* having the non-inflating bodies 34 around the elastic tubes 1*a* to 1 *d*, and a rigid tube 33 containing the non-inflating tubes 3*a* to 3*d* inside, as illustrated in FIG. 5, for example. (As the hollow portion of the elastic tube 1*a* communicates with that of the non-inflating tube 3*a*, they are collectively termed as tube A. The same applies to tube B and so on.)

(Overview of the Articulated Bending Portion)

The elastic tubes 1*a* to 1*d* forming the articulated bending portion each have a structure in which the flexible non-stretching body 4 fixed in the long-axis direction is embedded between the inner circumferential surface and the outer circumferential surface.

FIGS. 4(*b*) to 4(*e*) respectively show the elastic tubes 1*a* to 1*d* of the bending portion (joint) 31 in an inflated state due to the pressure of air W (fluid) injected from the control device 20. By thus pressurizing the individual elastic tubes, bends in four directions can be produced. Bend in an intermediate direction is also possible by selecting arbitrary two elastic tubes as shown in FIG. 4(*f*). Further, a rotational motion such as shown in FIG. 2(*c*) can also be produced by sequentially pressurizing the elastic tubes while adjusting the pressure.

FIG. 5 shows the cross-sectional structure of the non-bending portion 32. The non-inflating tubes 3*a* to 3*d* are structured by wrapping the non-inflating body 34 around the elastic tubes 1*a* to 1*d*. The outermost periphery of the non-bending portion 32 is formed of the rigid tube 33. Thus, the non-inflating tubes 3*a* to 3*d* do not inflate when the elastic tubes 1*a* to 1*d* are pressurized, so that the bending portions 31 can be bent without bending the non-bending portions 32.

The elastic tubes inside the non-inflating tubes 3*a* to 3*d* in the rigid tube 33 are not required to have the non-stretching body 4 in terms of their function because they already have the non-inflating bodies 34 around them as shown in FIG. 5. For convenience of fabrication, however, forming the non-stretching body 4 as an integral part in advance irrespective of bending or non-bending portions allows formation of bending portions 31 and non-bending portions 32 only with the presence or absence of the non-inflating body 34 and the rigid tube 33, and also increases the freedom of design. For this reason, all the elastic tubes in drawings are depicted in an exemplary structure including the non-stretching body 4.

(Overview of the Elastic Tube)

As shown in FIGS. 4(*a*) and 5, the elastic tube 1 includes an elastic tube body 11, the non-stretching body 4, and a fixing portion 13 for fixing the non-stretching body 4. The elastic tube body 11 is a primary component forming the elastic tube 1. The fixing portion 13 is provided in the long-axis direction of the elastic tube 1 and can fix the non-stretching body 4. While the non-stretching body 4 may be configured to be fixed to the outer or inner circumferential surface of the elastic tube by means of the fixing portion 13, it will be described here by taking an example where it is fixed being embedded between the outer and inner circumferential surfaces of the elastic tube body 11 (a thick wall portion) as shown in FIG. 4(*a*). The articulated bending portion 30 is formed of a set of four such elastic tubes 1 as a basic structure, and its tip on the side on which the endoscope camera 2 is mounted is sealed. A mounting portion for mounting the endoscope camera 2 is formed at the sealed tip of the articulated bending portion 30, enabling attachment of a medical device to the articulated bending portion 30. The medical device to be attached to the mounting portion is not limited to the endoscope camera 2 but may be a catheter, a laser scalpel, or an electric scalpel, for example. The mounting portion and the fixing portion 13 are parts of the elastic tube 1 and made of the same material as the elastic tube 1.

If the elastic tube body 11 has a structure with a uniform thickness for example, the portion in which the non-stretching body 4 is fixed particularly receives stress during pressurization and thus is easier to deteriorate locally. In a structure combining four elastic tubes 1 as shown in FIG. 4(*a*), a space is created between the tubes and the space can be utilized to make the thickness of the elastic tube body 11 in the portion where the non-stretching body 4 is fixed larger than the remaining portion, in which no non-stretching body 4 is fixed. This improves the durability of the fixing portion 13 and also increases the non-stretchability, providing the effect of achieving stable bending motions with no hysteresis to pressurization.

(Pressurization of Elastic Tubes)

Figure 6:
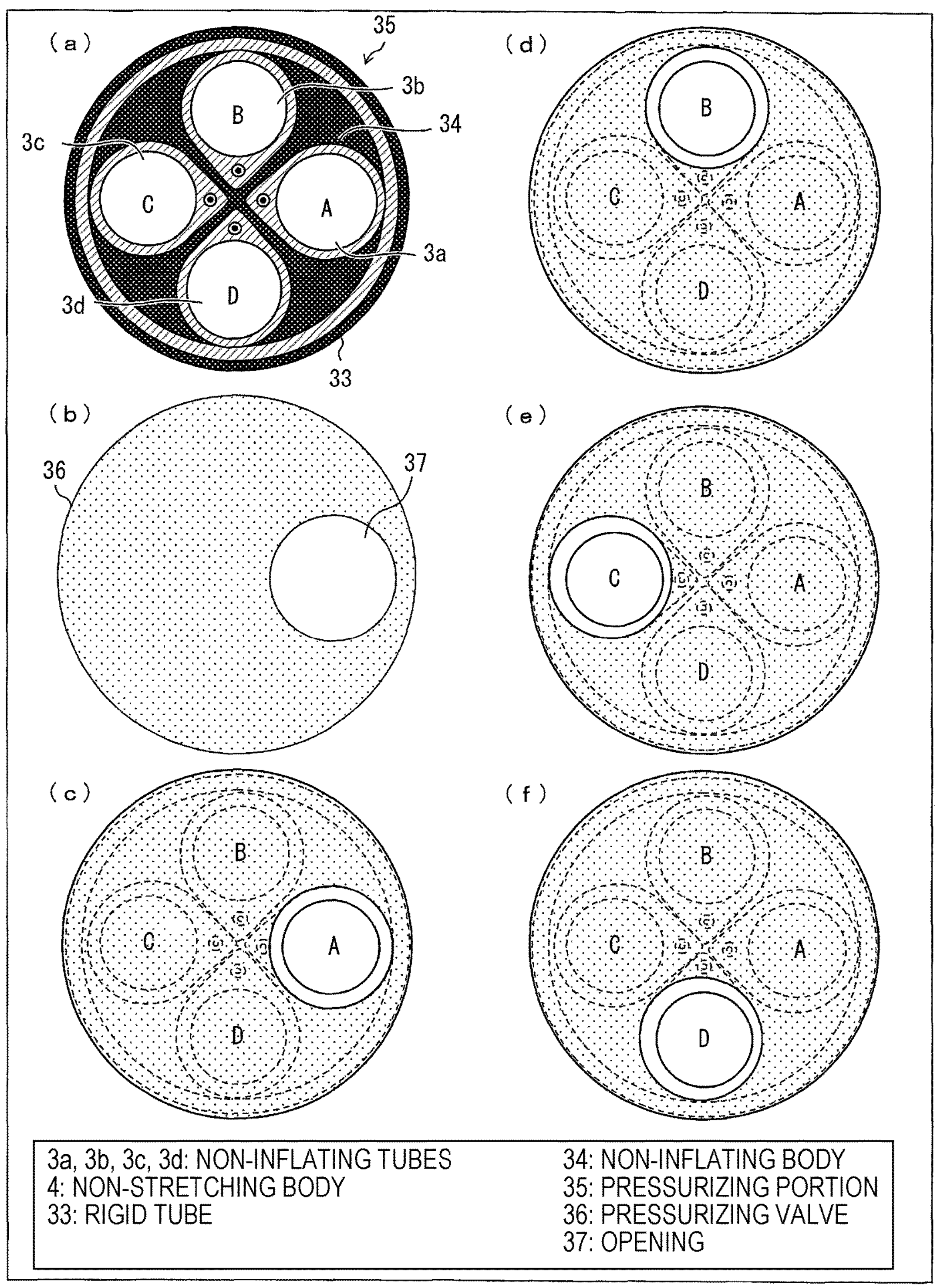
FIG. 6 shows cross-sectional views of the articulated bending portion, where FIG. 6(*a*) is a cross-sectional view showing an example of a pressurizing portion, FIG. 6(*b*) is a cross-sectional view of a pressurizing valve, and FIGS. 6(*c*) to 6(*f*) show examples of the arrangement position of the opening in the pressurizing valve.

Turning now to FIG. 6, an exemplary configuration of a pressurizing portion 35 for the elastic tubes 1 will be described. FIG. 6(*a*) shows an example for a relatively simple configuration with four elastic tubes 1, showing the cross section of the non-bending portion 32 at the proximal end of the articulated bending portion 30.

At the proximal end of the articulated bending portion 30, which refers to the end on the side of the control device 20, a pressurizing portion 35 for pressurizing the elastic tubes 1 is provided. As shown in FIG. 6(*a*), the proximal end is structured such that only the insides of the non-inflating tubes 3*a* to 3*d* are open and the remaining portion is sealed. In practice, a medical device such as an endoscope camera is attached to the distal end and thus cables for power supply and signals or the like are drawn from the side of the sealed portion, for example, though they are omitted in this drawing.

FIG. 6(*b*) shows an exemplary structure of a pressurizing valve 36, and FIGS. 6(*c*) to 6(*f*) show configurations in which the pressurizing valve 36 is disposed on the pressurizing portion 35.

By setting the pressurizing valve 36 shown in FIG. 6(*b*) on the pressurizing portion 35 and applying rotational movement to the pressurizing valve 36 as illustrated in FIGS. 6(*c*) to 6(*f*), pressure can be sequentially applied so as to pressurize only tube A, tubes A and B, only tube B, tubes B and C, only tube C, tubes C and D, tube D, and so on. In response to the rotation of the pressurizing valve 36, rotational movement of the endoscope camera 2 attached on the distal end can be produced as illustrated in FIG. 2(*c*).

This will be described more specifically. The pressurizing valve 36 has an opening 37. Tubes A, B, C, and D are supplied with and pressurized by air W from the control device 20, to be discussed later, through the opening 37. The pressurizing valve 36 rotates in response to control by the control device 20, so that the position of the opening 37 can be changed. A tube to be pressurized can be thereby selected and air W can be supplied to that tube.

Employing such a configuration can provide a straightforward and intuitively operable control mechanism in which the distal end portion rotates in synchronization with the rotation of the pressurizing valve.

Although the pressurizing valve 36 is described here as being connected to the proximal end of the articulated bending portion 30, this is not limitative and the pressurizing valve 36 may also be provided in a middle of a non-inflating tube 3 or the connecting tube 5 or a junction between them on the way of connection to the pressurization control device 20. Because an actuating mechanism for the valve is to be provided, the pressurizing valve 36 is desirably disposed in a proximal end portion close to the control device 20 as much as possible so that it does not interfere with a surgical procedure.

In addition, pressurizing portions may be provided at two or more locations, including a pressurizing portion for pressurizing the four tubes that drive the distal end portion and a pressurizing portion for pressurizing the four tubes that drive the middle to proximal end portions. This will be described in greater detail later as Embodiment 6.

Alternatively, instead of relying on the pressurizing valve structure described above, separate pressurization mechanisms may be provided for the respective tubes to independently control them so that fine position control allowing control to a desired position is performed in addition to rotation.

(Inflation of Elastic Tubes)

Using now FIGS. 3, 4, 10, and 11, inflation of the elastic tube 1 will be described in greater detail. FIG. 3(*a*) is a perspective view showing the primary components of the articulated bending portion 30, which constitutes the endoscope part 10 of the endoscope device 100 in FIG. 1. FIG. 4(*a*) is a cross-sectional view of the bending portion 31 of the endoscope part 10 in FIG. 3(*a*) as seen from the arrow in line A-A'. The elastic tube 1 shown in FIG. 4 is made of a silicone (polydimethylsiloxane with a reinforcing agent such as silicon oxide added) tube having an outer diameter of 2 mm, an inner diameter of 1 mm, and a length of 5 mm, for example. The elastic tube 1 inflates and deflates with the pressure of air W injected into the elastic tube 1 from the control device 20 (see FIG. 1). When the air W contained in the elastic tube 1 is at the atmospheric pressure (1 atm), the articulated bending portion 30, which is formed from such elastic tubes 1 as primary components, takes a linear shape as illustrated in FIG. 3(*a*). By increasing the pressure of air W contained in the elastic tube 1*a* (tube A), the elastic tube 1*a* (tube A) inflates in the bending portions 31 as shown in FIG. 3(*b*).

An LED lamp (not shown) for illumination may be attached adjacent to the mounting portion on which the endoscope camera 2 is attached. In the elastic tubes 1 shown in FIG. 3, illustration of the fixing portion is omitted for the convenience of description.

In FIG. 4(*a*), the non-stretching body 4 acts to prevent (suppress) the inflation of the elastic tube 1. Specifically, the elastic tube 1 does not inflate on the fixing portion side even when the portion of the elastic tube 1 that is on the opposite side of the fixing portion, in which the non-stretching body 4 is embedded and fixing (the middle upper side of the elastic tube 1*k* in FIG. 3(*a*)), inflates upon increase in the pressure of air W contained in the elastic tube 1. This enables the articulated bending portion 30 to curve downward in the drawing (to the opposite side of the inflated portion P) as illustrated in FIG. 3(*b*). Thus, by changing the pressure of air W in the elastic tube 1*a*, the curving angle of the articulated bending portion 30 can be changed as desired.

Using FIGS. 10 and 11, the behaviors of an elastic tube and an elastic tube positioned around it when the inside of the former elastic tube is pressurized will be described in detail.

Figure 10:
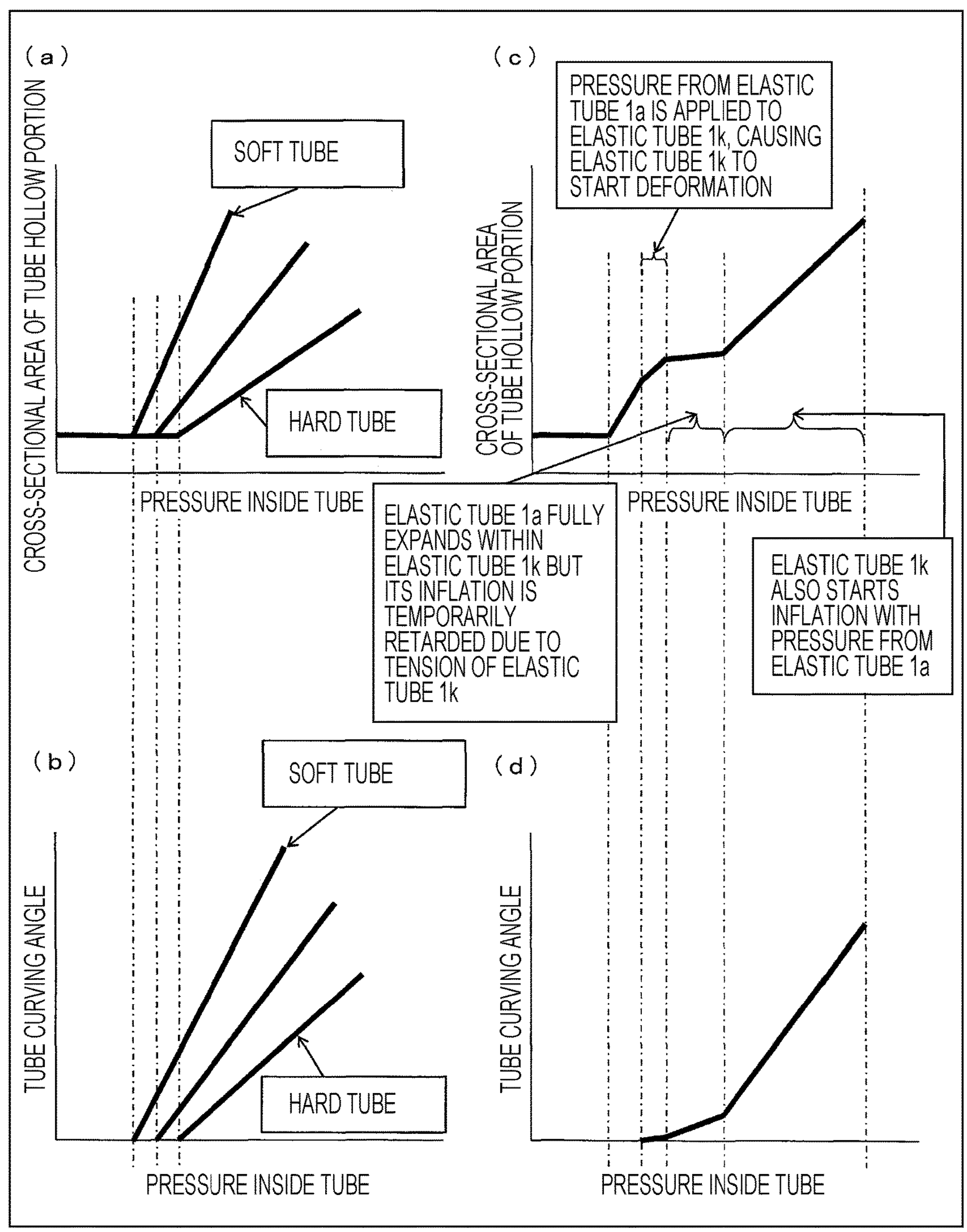
FIG. 10 shows graphs showing the relation between the internal pressure of an elastic tube according to Embodiment 1 of the present invention and the cross-sectional area of the hollow portion and the curving angle of the elastic tube.

First, a graph showing the relation between the internal pressure and the cross-sectional area of the hollow portion of a single elastic tube alone as a basic component when it is pressurized is provided in FIG. 10(*a*), and a graph showing the relation between the internal pressure and the curving angle is provided in FIG. 10(*b*). As shown in FIG. 10(*a*), as the elastic tube is pressurized, in the beginning, it does not inflate in response to the pressurization because of its tension, but starts to inflate at the point its internal pressure has exceeded the tension, causing the cross-sectional area to increase and also the elastic tube to start bending. The bending motion depends on the wall thickness of the elastic tube and the elastic modulus of its material. For instance, as shown in FIGS. 10(*a*) and 10(*b*), a soft tube starts bending at a low pressure and bends largely, whereas a hard tube starts bending at a relatively high pressure and makes a relatively small bend. Thus, bending motion characteristics of an elastic tube can be set as desired based on the configuration or the design of a material of the elastic tube.

Next, using FIGS. 10 and 11, a case of pressuring the inside of tube A in a bending portion 31 having the structure of FIG. 4 will be described as an illustrative example. FIG. 10(*c*) is a graph showing the relation between the internal pressure of tube A and the cross-sectional area of the hollow portion of tube A, and FIG. 10(*d*) is a graph showing the relation between the internal pressure of tube A and the curving angle of the elastic tube 1*k*.

Figure 11:
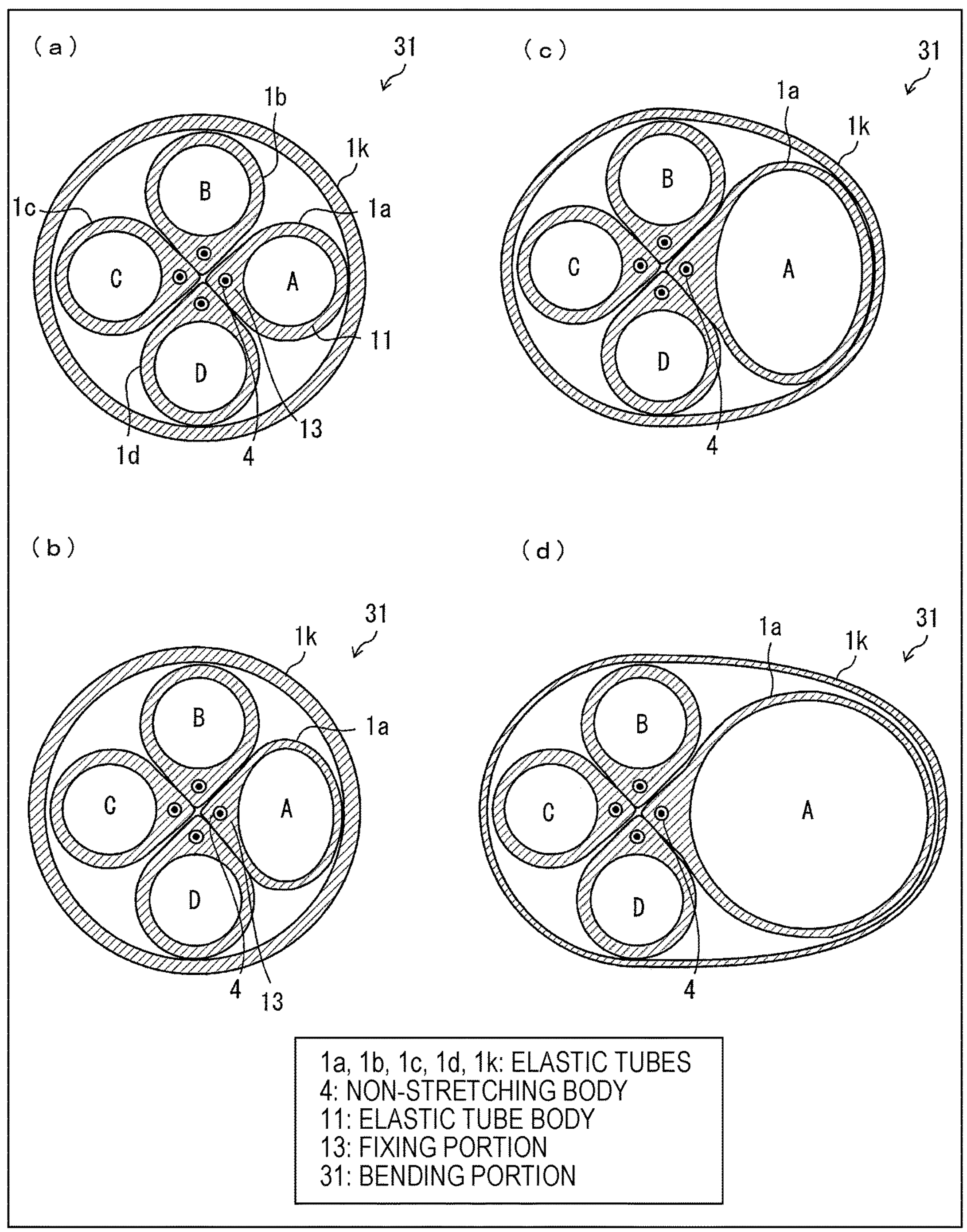
FIG. 11 shows cross-sectional views of the articulated bending portion according to Embodiment 1 of the present invention, sequentially illustrating states of tube A as it is pressurized.

As shown in FIG. 11(*a*), as tube A is pressurized, in the beginning, the elastic tube 1*a* portion does not inflate inside the elastic tube 1*k*, but at the point the tension of the tube itself has been exceeded, only the elastic tube 1*a* portion starts to inflate.

Then, as tube A is gradually pressurized as shown in FIG. 11(*b*), inflation of tube A (the elastic tube 1*a*) is temporarily retarded at the point when the pressure from the elastic tube 1*a* is applied to the elastic tube 1*k*.

As pressurization is further continued, the tube A and the elastic tube 1*k* start inflating at the same time as shown in FIG. 11(*c*), causing a substantial bend to start as shown in FIG. 11(*d*).

Accordingly, the relation between the internal pressure of tube A and the cross-sectional area of the hollow portion exhibits step-wise increase of the cross-sectional area as shown in FIG. 10(*c*). Further, the relation between the internal pressure of tube A and the curving angle exhibits a step-wise bending motion as shown in FIG. 10(*d*). That is, the bending angle of the elastic tube 1*k* changes stepwise in response to increase of the pressure inside tube A. As the bending motion is dependent on the size and wall thickness and the elastic modulus of the material of not only the elastic tube 1*a* but the elastic tube 1*k*, bending motion characteristics of these elastic tubes can be set as desired by arbitrarily setting the configurations and/or the structure of the materials of the elastic tubes.

Such a step-wise bending motion of the elastic tube 1*k* described above occurs not only during an increase of the internal pressure of tube A but during a decrease (drop) of the pressure.

Additionally, due to the presence of the elastic tube 1*k* on the outer periphery, such distinctive effect can be obtained that inflation in the elastic tube circumferential direction (the lateral direction), which does not contribute to bending, is suppressed and bending caused by inflation in the long-axis direction (the vertical direction), which directly affects the control of the curving angle, is effectively created. Further, since unnecessary inflation in the elastic tube circumferential direction is suppressed, degradation of the elastic tubes 1*a* to 1*d* caused by mechanical stress that occurs from repeated inflations and deflations can be prevented as well.

It is desirable that the air pressure W when the elastic tube is not bent be set to the pressure immediately before the elastic tube starts bending. This can prevent bending of the elastic tube caused by its own weight and keep the elastic tube in a straight linear shape.

The non-stretching body 4 has any stretchability lower than that of the elastic tube body 11 that is sufficient to allow the portion of the elastic tube body 11 opposite the fixing portion 13 (the thick wall portion on the opposite side of where the non-stretching body 4 is disposed) to inflate in the circumferential direction and prevent inflation of the elastic tube body 11 on the fixing portion 13 side. The material of the non-stretching body 4 may be non-stretching thread (fishing line) made of glass fiber or polyamide fiber, for example, or silicone, that is, the same material as the elastic tube 1.

The non-stretching body 4 may also be a cable connected with the medical device. For example, an electric cord for supplying power to the endoscope camera 2 may double as the non-stretching body 4 shown in FIG. 4(*a*). Alternatively, a cable that connects between the endoscope camera 2 and a camera monitor (not shown) along the endoscope part 10 shown in FIG. 1 may double as the non-stretching body 4. The non-stretching body 4 and a cable connected with the medical device may be fixed inside the elastic tube body 11.

(Connection from the Articulated Bending Portion to the Control Device)

The non-inflating tube 3 is formed of a linear, hard hollow member having a length of about 2 cm to 30 cm (which is not limitative and the length is desirably set to an appropriate size depending on the number of joints) that has the same shape as the articulated bending portion 30, namely the same outer and inner diameters as the elastic tube body 11. The non-inflating tube 3 may be fabricated from acrylic resin.

In FIG. 1, the connecting tube 5 is a tube connecting between the endoscope part 10 and the control device 20. The connecting tube 5 is a hollow, cylindrical tube which is flexible and non-inflatable, and is connected with the non-inflating tube 3. The connecting tube 5 has a shape substantially the same as the non-inflating tube 3 and is about 2 m long, communicating with the elastic tube 1 and the non-inflating tube 3. The connecting tube 5 contains air W. The non-bending portion 32 at the proximal end side may be held on a flexible stand. This would permit the direction of the articulated bending portion 30 to be changed as desired using the flexible stand.

The connecting tube 5 may consist of multiple connecting tubes, depending on the configuration of the pressurization mechanism for the elastic tubes.

(Hollow Interior of the Elastic Tube)

FIG. 3(*c*) is a cross-sectional view of the elastic tube 1*a* as an example and the non-inflating tube 3*a* in the long-axis direction as seen from the arrow in line C-C' in FIG. 3(*a*). As shown in FIGS. 3(*c*) and 5, the non-inflating tube 3*a* is structured by wrapping the non-inflating body 34 around the elastic tube 1*a*.

FIG. 3(*d*) shows another example of the structure of the elastic tube 1*a* and the non-inflating tube 3*a*. As shown in FIG. 3(*d*), the elastic tube 1*a* and the non-inflating tube 3*a* may be separate components which are coupled together by bonding such that their hollow portions communicate with each other. (As the hollow portion of the elastic tube 1*a* communicates with that of the non-inflating tube 3*a*, they are collectively termed as tube A. The same applies to tube B and so on.) The hollow portion of the elastic tube 1*a* and so on contains air W supplied by the control device 20 from the side of the connecting tube 5 through the non-inflating tube 3.

The non-stretching body 4 is very thin relative to the elastic tube body 11; for example, when the outer diameter of the elastic tube body 11 in cross section is 2 mm, the outer diameter of the non-stretching body 4 in cross section is about 0.3 to 0.5 mm. The cross section of the non-stretching body 4 is not limited to a circular shape but may be a polygonal shape, such as a triangle or square, that is chamfered so as not to damage the human body when inserted into the body and small in size.

Although not shown, the elastic tube 1 may also be structured such that the fixing portion 13 (not shown) is positioned on the outer circumferential surface (the exterior) of the elastic tube body 11. In that case, the non-stretching body 4 is fixed to the exterior of the elastic tube body 11.

If a cable connected with a medical device (for example, an electric cord) doubles as the non-stretching body 4, the non-stretching body 4 (or the electric cord) is bonded to the side surface of the non-inflating tube 3 (see FIG. 1) in addition to the fixing portion 13 of the elastic tube 1, and drawn outside the endoscope part 10.

The elastic tube may also be structured such that the fixing portion is positioned on the inner circumferential surface (the interior) of the elastic tube body 11. In that case, the non-stretching body 4 is fixed to the interior of the elastic tube body 11. A cable connected with a medical device may also double as the non-stretching body 4.

With such a configuration, because the non-stretching body 4 and the cable connected with the medical device are fixed on the interior of the elastic tube body 11, no unevenness would occur on the surface of the elastic tube body 11 if the elastic tubes are exposed on the outermost surface. This makes the elastic tube 1*k* easy to wash and sterilize, facilitating its reuse.

In addition, with the aforementioned configuration, the non-stretching body 4 and the cable connected with the medical device are fixed on the interior of the elastic tube body 11, thus placed in locations protected by the elastic tube body 11. Accordingly, if part of the non-stretching body 4 and the cable connected with the medical device is broken for some reason, the broken part is protected by the elastic tube body 11, thus lowering the risk of damage to the human body. For example, if part of the non-stretching body 4 is broken for some reason, the risk of the broken part of the non-stretching body 4 damaging the human body is low even when the non-stretching body 4 has lower stretchability than the elastic tube. As another example, if the cable connected with the medical device is an electric cable, adverse effects such as current leakage due to breakage of the electric cable can be avoided in the human body. Besides, since gas is injected in the elastic tube body 11, should the electric cable is broken, adverse effects of current leakage can be avoided in the elastic tube body 11 because electrical conductivity in the elastic tube body 11 is low.

In a case where a non-stretching body 4 different from the cable connected with the medical device is fixed to the elastic tube body 11, the cable connected with the medical device may be disposed in the hollow interior of the elastic tube body 11. For instance, in a case where the fixing portion is disposed on the inner circumferential surface (the interior) of the elastic tube body 11, a non-stretching body 4 different from the cable connected with the medical device may be fixed on the interior of the elastic tube body 11 and the cable connected to the medical device may be disposed in the hollow interior of the elastic tube body 11.

The elastic tube may also be structured such that the fixing portion is disposed inside the elastic body of the elastic tube body 11. The elastic body is the constituent of the elastic tube body 11, forming the thickness portion from the inner circumferential surface to the outer circumferential surface of the elastic tube body 11. More specifically, the elastic tube is structured such that the fixing portion is disposed between the inner circumferential surface and the outer circumferential surface of the elastic tube body 11. Accordingly, the non-stretching body 4 is fixed so as to be embedded between the inner circumferential surface and the outer circumferential surface of the elastic tube body 11. That is, an elastic tube body 11 having such a structure permits the non-stretching body 4 to be fixed to the elastic tube body 11 by advance formation of the non-stretching body 4 as an integral part of the elastic tube body 11. A cable connected with a medical device may double as the non-stretching body 4 as well.

In a case where the non-stretching body 4 is provided separately from a cable connected with a medical device, the non-stretching body 4 may be fixed so as to be embedded between the inner circumferential surface and the outer circumferential surface of the elastic tube body 11, and the cable may be disposed in the hollow interior of the elastic tube body 11. In addition, although the non-stretching body 4 or the cable may be configured to be in contact with the outer circumferential surface and inner circumferential surface of the elastic tube body 11, it is desirable that they be disposed spaced apart from the outer circumferential surface or inner circumferential surface of the elastic tube body 11 in order to enhance the mechanical strength of the elastic tube.

With the foregoing configuration, the non-stretching body 4 and the cable connected with the medical device are embedded between the inner circumferential surface and the outer circumferential surface of the elastic tube body 11, so no unevenness would occur on the surface (the outer circumferential surface) of the elastic tube body 11. This makes the elastic tubes easy to wash and sterilize to facilitate their reuse even when the elastic tubes are exposed on the outermost surface.

With the above-described configuration, the non-stretching body 4 and the cable connected with the medical device are in locations protected by the elastic tube body 11 because they are fixed between the inner circumferential surface and the outer circumferential surface of the elastic tube body 11 or to the hollow interior of the elastic tube body 11. Thus, if part of the non-stretching body 4 and the cable connected with the medical device is broken for some reason, the broken part is protected by the elastic tube body 11, thus lowering the risk of damage to the human body.

For example, if part of the non-stretching body 4 is broken for some reason, the risk of the broken part of the non-stretching body 4 damaging the human body is low even when the non-stretching body 4 has lower stretchability than the elastic tube. As another example, if the cable connected with the medical device is an electric cable, adverse effects such as current leakage caused by breakage of the electric cable can be avoided in the human body. Besides, since gas is injected in the elastic tube body 11, should the electric cable is broken, adverse effects of current leakage can be avoided in the elastic tube body 11 because electrical conductivity in the elastic tube body 11 is low.

In addition, with the foregoing configuration, the outer circumferential surface of the non-stretching body 4 or the cable connected with the medical device is entirely fixed to the elastic tube body 11. Thus, the curving angle □ of the elastic tube changes at a constant rate in relation to the level of the pressure P of the air present in the hollow interior of the elastic tube body 11. This provides the advantage of facilitating the control of the curving angle □ of the elastic tube body 11.

With the foregoing configuration, the aforementioned adverse effects on the human body that could be caused by the cable connected to the medical device can be avoided. Further, because the portion around the medical device mounted to the elastic tube 1 can be made compact, a cable connected with the medical device will not interfere with a medical procedure.

(Overview of the Control Device)

The control device 20 in FIG. 1 will be described. Note that the following description presents an example of the control device 20 and is not intended to limit the configuration of the control device. The control device 20 can have any of various configurations that are capable of pressurizing the tubes contained in the articulated bending portion 30, without being limited to the configuration described below.

The control device 20 includes a piston (air pressure varying unit, a fluid pressure varying unit) 21 and a syringe 22 for changing the pressure of air (gas) W in the elastic tube 1, an air pressure sensor 23 for detecting the pressure of air W, a piston driving unit (an air pressure varying unit) 24 for actuating the piston 21 in the syringe 22 and varying the air pressure in the elastic tube 1, a microphone (an instruction receiving unit) 25 to which voice of the operator (instructions) is input, and a pressurization control unit (an air pressure varying unit) 26 for controlling the piston driving unit 24. The pressurization control unit (air pressure varying unit) 26 may be configured to receive voice signals input through the microphone 25, and detection signals from the air pressure sensor 23 as input and control the piston driving unit 24, for example. The gas contained in the elastic tube 1 is not limited to air, but can be any kind of gas that does not contaminate the treated site.

The control device 20 also includes a pressurizing valve driving unit 28. The pressurizing valve driving unit 28 rotates the pressurizing valve 36 in response to control by the pressurization control unit 26.

While this embodiment uses the piston 21, piston driving unit 24, and pressurization control unit 26 as examples of air pressure varying units, they may be replaced with an air pressure regulating valve or the like. Also, a foot switch or the like may be used instead of the microphone.

(Manipulation Through the Control Device)

A scenario in a medical procedure (an operation) will be described below. In response to the voice of the operator detected by the microphone, the pressurization control unit 26 controls the piston driving unit 24 so as to change the air pressure in the elastic tube 1 using the piston 21 and the syringe 22.

For instance, in a situation where the endoscope camera 2 is able to curve upward or downward on the display screen of a camera monitor, if the operator says "up", the image being displayed on the display screen of the camera monitor starts to move so as to show the upper side of the image. Then, in response to the operator saying "stop", the image on the display screen of the camera monitor stops moving. If the operator says "down", the image being displayed on the display screen of the camera monitor moves downward.

After being used in a medical procedure or the like, the elastic tube 1 can be replaced with a new elastic tube 1 (that is, is disposable). Alternatively, a used elastic tube 1 can be used again (reused) after completion of a medical procedure by washing and disinfecting it. When elastic tubes 1 are reused, for preventing use of degraded elastic tubes 1, it is required to preset an upper limit number of times the elastic tube 1 can be used or curved in the control device 20 and prohibit use of an elastic tube 1 that has been used or curved the upper limit number of times.

(Specific Example of the Control Device)

The piston 21 is slidably inserted in the syringe 22 connected with connecting tube 5. The piston 21 may also be configured to be fit on a screw portion coupled to the piston driving unit 24 so that the piston driving unit 24 makes the piston 21 slide within the syringe 22 by rotating the screw portion positively or negatively. Whether the piston driving unit 24 rotates positively or negatively and the number of rotations are controlled by the pressurization control unit 26.

(Curving Angle of the Elastic Tube)

The curving characteristics of the elastic tube in an embodiment of the present invention will be described below based on the relation between the air W present in the elastic tube body 11 and the curving angle of the elastic tube body 11.

First, they will be described by taking as an example a configuration in which the non-stretching body 4 is fixed to the outer circumferential surface or the inner circumferential surface of the elastic tube body 11.

For example, when the pressure P of air W in the elastic tube body 11 is increased (during pressurization), the curving angle □ of the elastic tube 1 gently increases monotonously in response to increase of the air pressure until the pressure is around 230 kPa. After the pressure P has increased past around 230 kPa, the curving angle □ of the elastic tube 1 sharply increases relative to increase in pressure P. When the pressure P of air W in the elastic tube body 11 is decreased (during depressurization), the curving angle □ of the elastic tube 1 gently decreases monotonously in response to decease in pressure P until the pressure P is around 230 kPa. After pressure P decreased below around 230 kPa, the curving angle □ of the elastic tube body 11 sharply decreases relative to decrease of pressure P until the pressure P is around 170 kPa. Then, after pressure P has decreased below around 170 kPa, the curving angle □ of the elastic tube body 11 again gently decreases monotonously in response to decrease in pressure P.

By presetting such curving characteristics of the elastic tube body 11 in the pressurization control unit 26, the curving angle of the elastic tube body 11 can be changed so that the image being displayed on the camera monitor moves at a constant rate.

Next, the curving characteristics will be described by taking a case where the non-stretching body 4 is fixed so as to be embedded between the inner circumferential surface and the outer circumferential surface of the elastic tube body 11 as an example.

For example, when the pressure P of air W in the elastic tube body 11 is increased (during pressurization), the curving angle □ of the elastic tube 1*b* increases almost linearly in response to increase in the air pressure from a pressure of around 100 kPa to around 260 kPa. When the pressure P of air W in the elastic tube body 11 is decreased (during depressurization), the curving angle □ of the elastic tube 1*b* linearly decreases in response to decrease in pressure P from a pressure P of around 260 kPa to around 100 kPa.

As shown above, during both pressurization and depressurization, the curving angle □ of the elastic tube 1*b* changes at a corresponding constant rate each time there is an increase or decrease in pressure P, without causing large hysteresis characteristics. Also, the relation between pressure P and angle □ during pressurization is substantially equal to the relation between pressure P and angle □ during depressurization.

By presetting such curving characteristics of the elastic tube body 11 in the pressurization control unit 26, the curving angle of the elastic tube body 11 can be changed so that the image being displayed on the camera monitor moves at a constant rate. Moreover, since the curving characteristics of the elastic tube body 11 are linear in the above example, setting of the pressurization control unit 26 will be simpler when an elastic tube body 11 with linear characteristics is used than when an elastic tube 1 with hysteresis characteristics is used. This provides the advantage of facilitating the control of the curving angle of the elastic tube body 11.

(Exemplary Manipulation of the Elastic Tube)

The elastic tube 1 may also be adapted for automated manipulation. For example, if the endoscope camera 2 shown in FIG. 1 is used as a medical device, an arrangement (not shown) may be employed in which an image captured by the endoscope camera 2 is displayed on the camera monitor and at the same time the image captured by the endoscope camera 2 is acquired and analyzed by the control device 20. The control device 20 automatically adjusts the pressure of the gas contained in the elastic tube body 11 based on information analyzed. The curving angle of the endoscope camera 2 thus can be changed in an automated manner. The control device 20 has prestored therein image data indicative of the progress of a medical procedure or the like. The control device 20 may also change the curving angle of the endoscope camera 2 using the hysteresis characteristics described above.

The elastic tube 1 may also be manually operated using a tablet terminal. For example, when an assistant of the operator conducting a medical procedure manipulates a tablet terminal to change the curving angle of a medical instrument, the assistant can manipulate the tablet terminal at a location away from the operator. Thus, manipulation by the assistant does not interfere with the medical procedure actions being performed by the operator, allowing the operator to concentrate on the medical procedure. Alternatively, the operator may manipulate a tablet terminal to change the curving angle of the medical instrument, for example. In such a case, a robot can be made perform the actual medical procedure on behalf of the operator.

Embodiment 2

Another embodiment of the present invention will be described below based on FIGS. 7 to 9. For the sake of description, components having the same functionality as ones described in the previous embodiment are denoted with the same reference characters and description of such components is omitted.

Embodiment 1 mainly described a movable mechanism with a single bending portion in detail, while Embodiment 2 will describe a movable mechanism that operates by coordinating two bending portions in combination.

(Overview of the Articulated Bending Portion)

Figure 7:
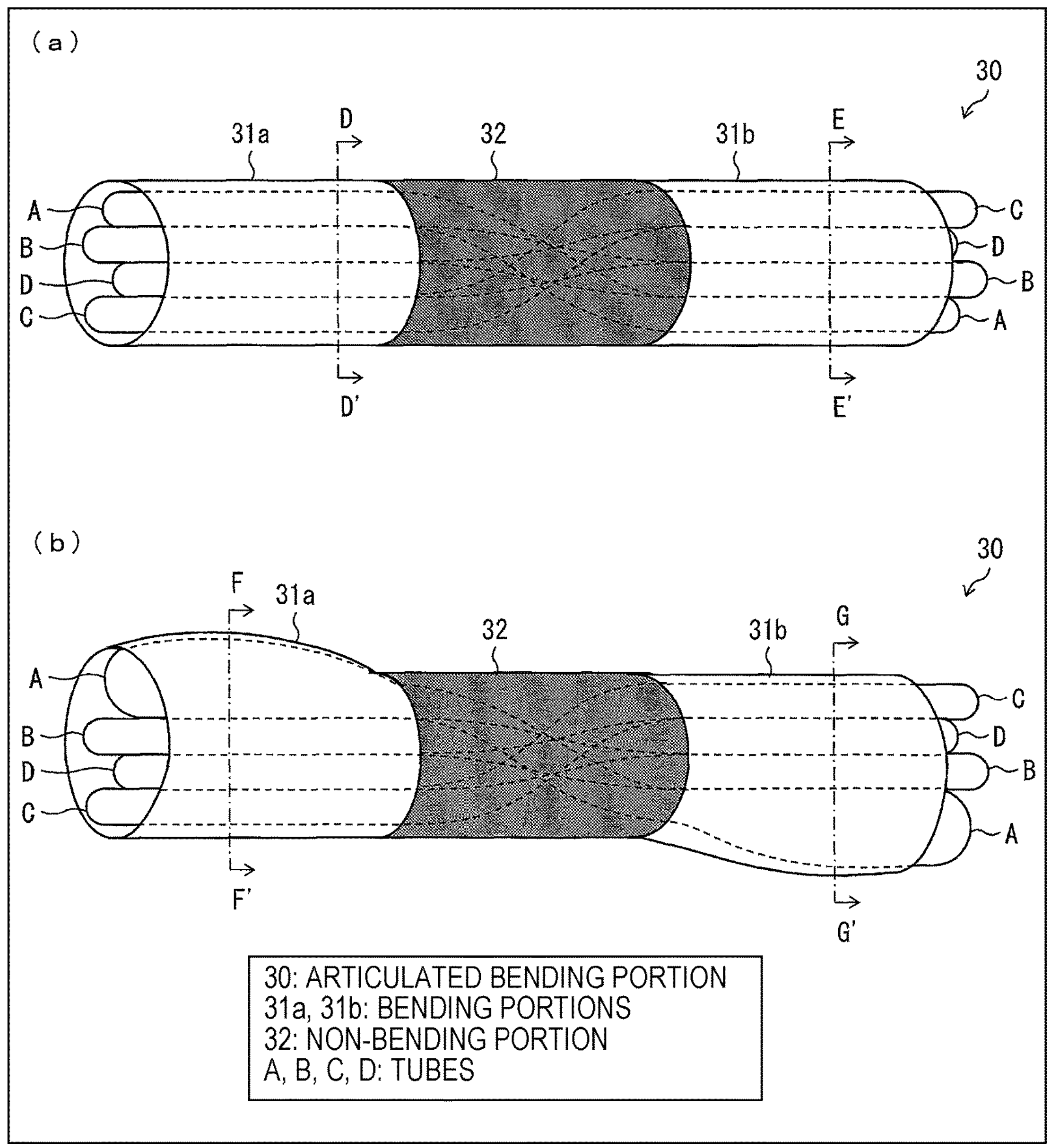
FIG. 7 shows perspective views showing an example of the internal structure of bending portions and a non-bending portion of the articulated bending portion according to Embodiment 2 of the present invention, where FIG. 7(*a*) illustrates a non-bent state and FIG. 7(*b*) illustrates a bent state.

FIG. 7 shows an example of a movable mechanism that operates by coordinating two bending portions in combination. While the configuration with four elastic tubes 1*a* to 1*d* forming the articulated bending portion is similar to Embodiment 1, the position of each of the elastic tubes 1*a* to 1*d* is interchanged with the opposite tube in the non-bending portion 32 as illustrated in FIG. 7.

Figure 8:
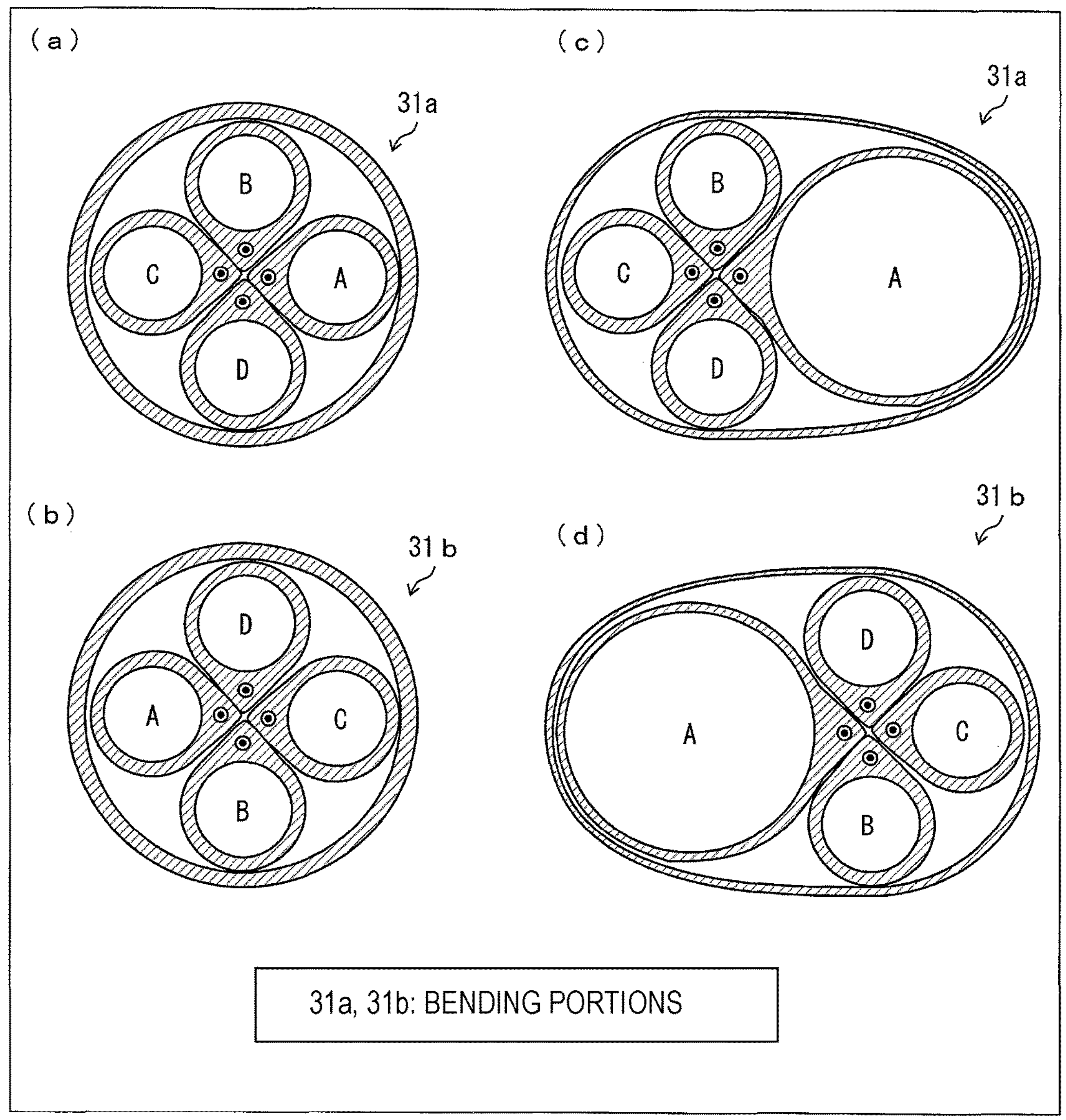
FIGS. 8(*a*) to 8(*d*) are cross-sectional views of the articulated bending portion in Embodiment 2.

FIG. 8(*a*) is a cross-sectional view seen from the arrow in line D-D' in FIG. 7(*a*); FIG. 8(*b*) is a cross-sectional view seen from the arrow in line E-E' in FIG. 7(*a*); FIG. 8(*c*) is a cross-sectional view seen from the arrow in line F-F' in FIG. 7(*b*); and FIG. 8(*d*) is a cross-sectional view seen from the arrow in line G-G' in FIG. 7(*b*).

As an example, as shown in the cross-sectional views of FIGS. 8(*a*) and 8(*b*), the elastic tube 1*a* can be interchanged with 1*c* and also 1*b* can be interchanged with 1*d*. This can be considered as a characteristic feature enabled by independent elastic tubes.

As shown in FIGS. 7(*b*), 8(*c*), and 8(*d*), for example, when the elastic tube 1*a* is pressurized with the pressure of air W injected from the control device 20, inflation in opposite directions occurs in the bending portions (joints) 31*a* and 31*b*. Thus, bends in opposite directions can be produced in two bending portions as illustrated in FIGS. 9(*a*) and 9(*b*).

By making settings so that the bending angles of the two bending portions are the same, the distal end portion can be steered without changing the orientation of the distal end portion unlike Embodiment 1. This provides a distinctive effect of yielding an image very easy for the operator to see especially when the distal end portion is equipped with a camera because the field of view can be moved without changing the angle of view.

Also, similarly to Embodiment 1, as the bending motions in the two bending portions 31*a* and 31*b* are dependent on the size and wall thickness, the elastic modulus of the material, and the self-weight of not only the elastic tube 1*a* but the elastic tube 1*k*, the elastic tubes can be designed to have the same bending motion characteristics by appropriately setting the configurations and/or the material structures of the elastic tubes.

Additionally, due to the presence of the elastic tube 1*k* on the outer periphery, such distinctive effect can be obtained that inflation in the elastic tube circumferential direction (the lateral direction), which does not contribute to bending, is suppressed and bending caused by inflation in the long-axis direction (the vertical direction), which directly affects the control of the curving angle, is effectively created. Further, since unnecessary inflation in the elastic tube circumferential direction is suppressed, degradation of the elastic tubes 1*a* to 1*d* caused by mechanical stress that occurs from repeated inflations and deflations can be prevented as well.

As in Embodiment 1, bends in four directions can be produced by pressurizing the individual elastic tubes, and further a bend in an intermediate direction is also possible by selecting arbitrary two elastic tubes. That is, a rotational motion of the distal end portion such as shown in FIG. 9(*b*) or movement of the field of view in a desired direction can also be achieved by sequentially pressurizing the elastic tubes while adjusting the pressure.

Figure 9:
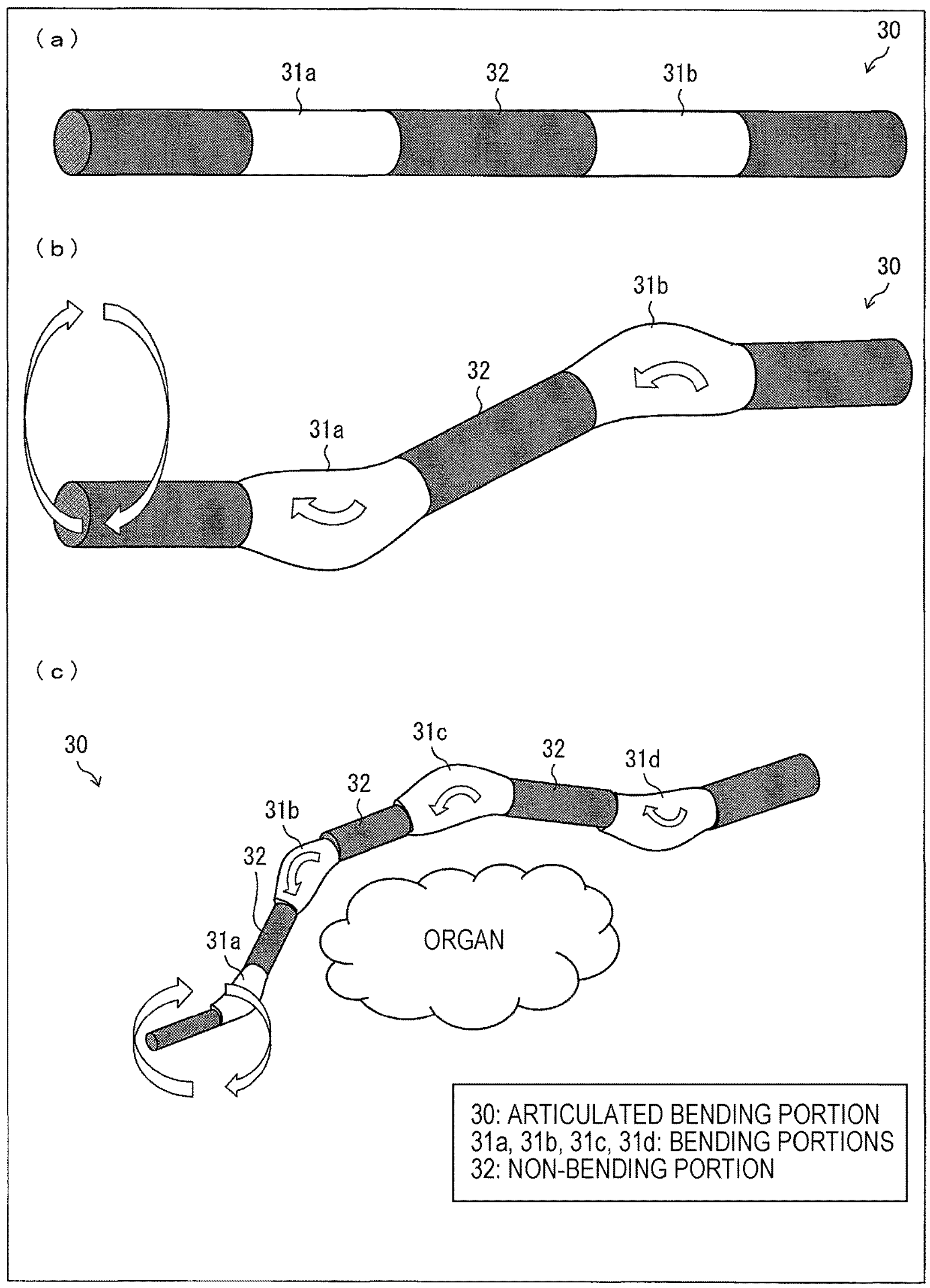
FIGS. 9(*a*) to 9(*c*) are perspective view illustrating the bending motion of the articulated bending portion in Embodiment 2.

As shown in FIG. 9(*c*), a set of bending portions 31 bend in a particular direction depending on the positions of the tubes incorporated therein in advance. For example, bends in opposite directions can be produced by interchanging the positions of the elastic tubes 1*a* to 1*d* with the opposite tubes in a non-bending portion 32 as described above, or bends shifted by 90 degrees can be produced by interchanging each tube with a neighboring tube.

For such multiple bending points, the pressure at which they start bending may be adjusted by appropriately combining the aforementioned various features so that bending motions simultaneously occur in all of the bending points or bends occur sequentially starting from the bending point at the distal end, for example.

In this way, a variety of bending directions and bending motions are possible based on the combination of the positions and bending characteristics of the tubes incorporated in advance and the amount of pressurization for the four tubes. Specifically, by combining them with insertion or removal of pipes themselves and/or rotational motions, a wide variety of bending motions such as avoiding an organ or going behind an organ and viewing an object area from the back side (upward avoidance, rightward avoidance, leftward avoidance, or change of avoidance joint position) can be achieved. Specific examples of a wide variety of bending motions will be described in detail later in Embodiments 6 and 7.

Embodiment 3

Still another embodiment of the present invention will be described below based on FIGS. 12 to 14. For the sake of description, components having the same functionality as ones described in the previous embodiments are denoted with the same reference characters and description of such components is omitted.

Embodiments 1 and 2 mainly detailed a movable mechanism in which another elastic tube (referred to below as an "outer peripheral elastic tube") is disposed on the outer periphery of elastic tubes pressurized for producing a bending motion and which has one or two bending portions, particularly in connection with application to a distal end portion having a camera attached thereon, while Embodiment 3 will describe a movable mechanism that operates with a plurality of outer peripheral elastic tubes.

Here, this embodiment describes an example in which a movable mechanism is configured to include a plurality of outer peripheral elastic tubes. However, not limited to this, the movable mechanism may be configured to have any multi-layer structure. Further, the multi-layer structure also includes the configuration in which a single outer peripheral elastic tube is provided on the outermost periphery and at least one anisotropically-stretchable elastic body, which does not have a tubular structure and will be described later, is provided inside the outer peripheral elastic tube. Furthermore, the configuration in which an anisotropically-stretchable elastic body is provided between the inner circumferential surface and the outer circumferential surface of a single outer peripheral elastic tube is also included.

(Overview of the Articulated Bending Portion)

Figure 12:
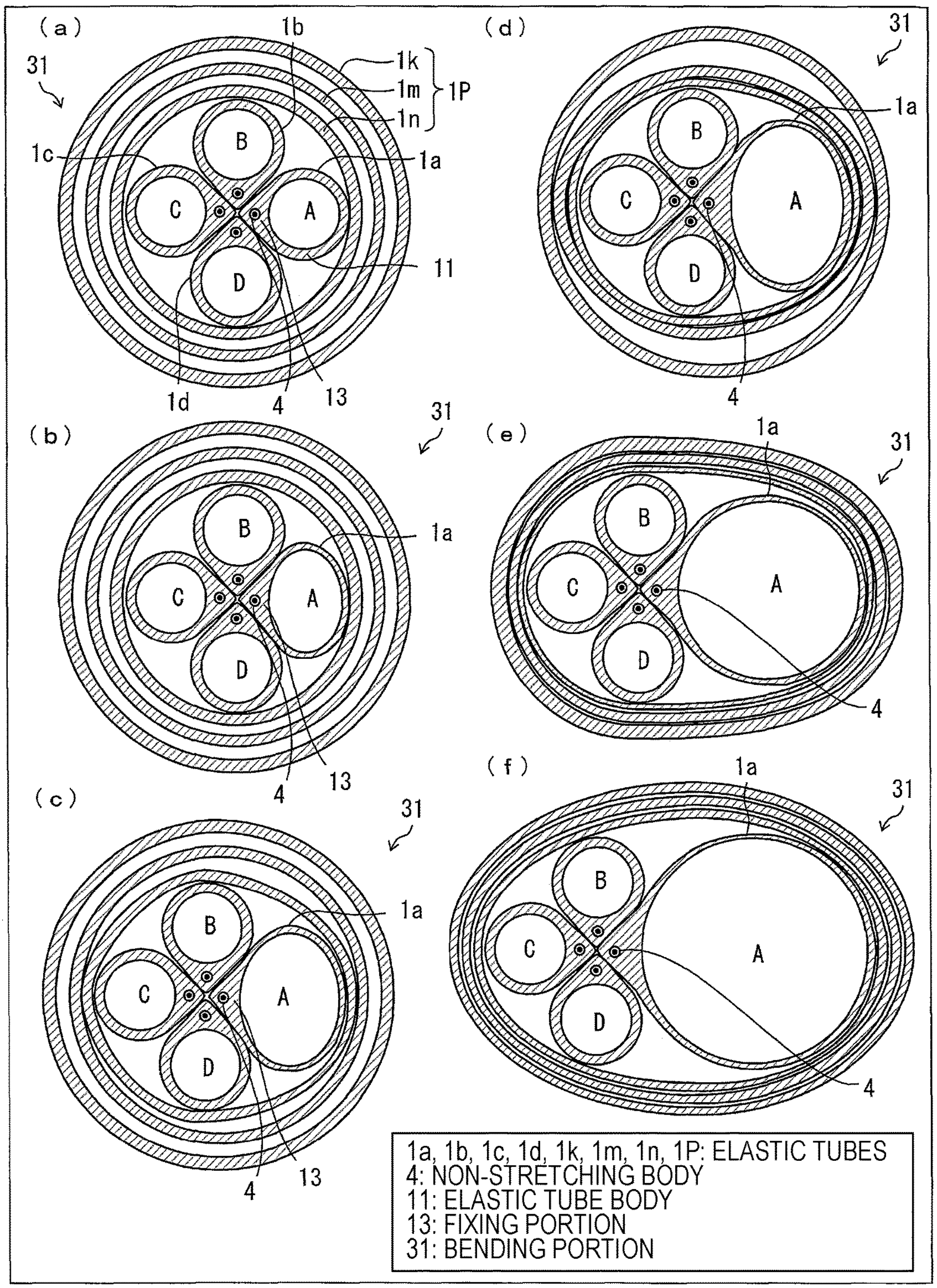
FIGS. 12(*a*) to 12(*f*) show cross-sectional views of the articulated bending portion according to Embodiment 3 of the present invention, sequentially illustrating states of tube A as it is pressurized.

FIG. 12 shows an example of a bending portion having the configuration with outer peripheral elastic tubes triply provided. Here, the number of the outer peripheral elastic tubes is not limited to this but the configuration with arbitrary number of outer peripheral elastic tubes may be employed.

As the configuration in this example is the same as the configuration shown in FIG. 11 other than the triply-provided outer peripheral elastic tubes, detailed descriptions of tubes A to D already described in Embodiments 1 and 2 will be omitted.

Using FIGS. 12 and 13, the behaviors of tube A and outer peripheral elastic tubes 1*k* to 1*n* when the inside of tube A is pressurized will be described in detail. The cross-sectional structure of the bending portion 31*b* is shown in FIG. 12(*a*). As shown in FIG. 12(*a*), the elastic tube 1P (tubular member) has a nested structure in which the elastic tube 1*m* (outer peripheral elastic tube) is housed in the elastic tube 1*k* (outer peripheral elastic tube) positioned outermost and the elastic tube 1*n* (outer peripheral elastic tube) is housed further inside. The elastic tubes 1*k*, 1*m*, and 1*n* have inner diameters different from each other and accordingly, the elastic tubes 1*k*, 1*m*, and 1*n* mutually have gaps of predetermined widths. As shown in FIG. 12(*a*), the elastic tube 1P has a triply-layered structure that is formed from three elastic tubes 1*k*, 1*m*, and 1*n*, in the shape of the cross section orthogonal to the axis direction of the elastic tube 1P.

Figure 13:
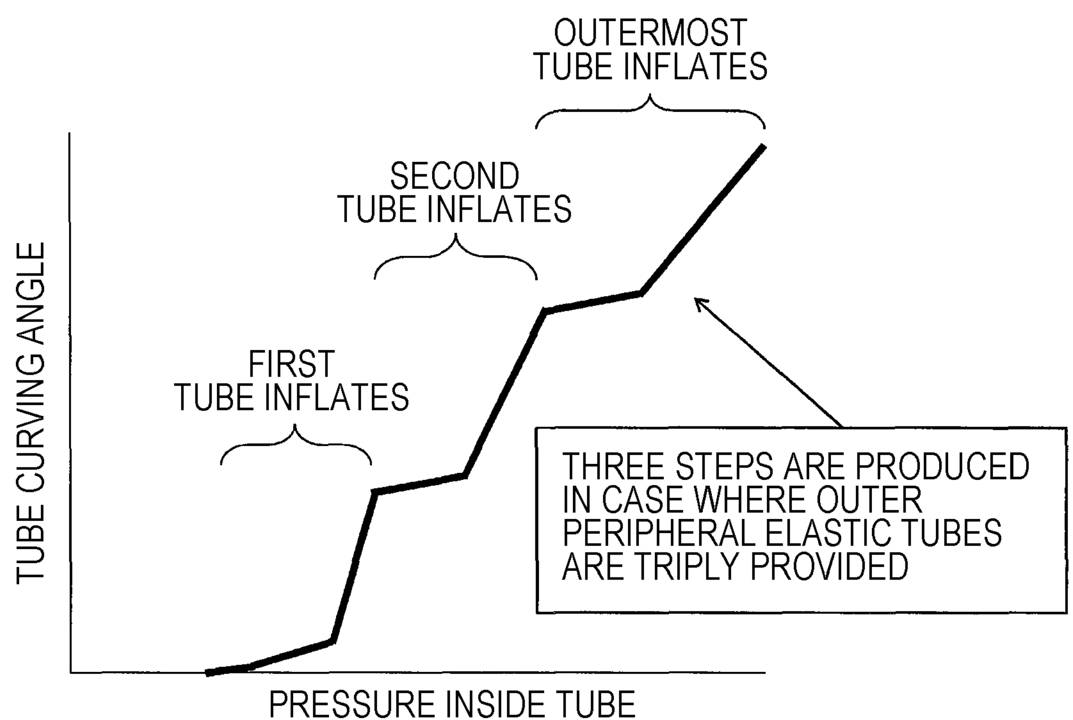
FIG. 13 is a graph showing the relation between elastic tube internal pressure and a curving angle of an articulated bending portion according to Embodiment 3 of the present invention.

FIGS. 12(*b*) to 12(*f*) sequentially show a state change of the bending portion 31*b* when the inside of tube A is pressurized, and FIG. 13 is a graph showing the relation between internal pressure of tube A and a curving angle of the bending portion 31*b* in the case.

As shown in FIG. 13, as the inside of tube A is pressurized, in the beginning, only a portion of the elastic tube 1*a* inflates inside the elastic tube 1*n* and curving is not produced.

Then, as shown in FIG. 12(*b*), at the point when pressure from the elastic tube 1*a* is applied to the elastic tube 1*n* after gradual pressurization, the tension of the tube 1*n* is applied and thus inflation of the elastic tube 1*a* is started being temporarily retarded.

As pressurization is further continued, the elastic tube 1*n* deforms in an elliptic shape along with inflation of tube A, as shown in FIG. 12(*c*). Until the internal pressure of tube A exceeds the tension of the tube 1*n*, the above-mentioned state in which inflation is temporarily retarded is continued.

As the pressurization is further continued and when the internal pressure of tube A exceeds the tension of the tube 1*n*, tube A and the elastic tube 1*n* simultaneously start inflating again and the elastic tube 1*m* deforms in an elliptic shape to start temporarily retarding inflation of the elastic tubes 1*a* and 1*n* this time, as shown in FIG. 12(*d*).

As the pressurization is further continued and when the internal pressure of tube A exceeds the tension of the tube 1*m*, tube A and the elastic tubes 1*n* and 1*m* simultaneously start inflating again, as shown in FIG. 12(*e*). As the pressurization is further continued, inflation and bending of the bending portion 31*b* progress ultimately, as shown in FIG. 12(*f*).

Accordingly, the relation between the internal pressure of tube A and the curving angle exhibits such that inflation is retarded at the point when pressure is applied to the outer peripheral tube to produce the bending motion having three stages corresponding to the number of elastic tubes included in the elastic tube 1P, as shown in FIG. 13.

As the bending motion is dependent on the size and wall thickness and the elastic modulus of the materials of not only the elastic tube 1*a* but the elastic tubes 1*k*, 1*m*, and 1*n*, bending motion characteristics of these elastic tubes can be set as desired by arbitrarily setting the configurations and/or the structure of the materials of the elastic tubes. For example, the materials of respective elastic tubes may be set so that at least one of the elastic tubes 1*k*, 1*m*, and 1*n* has different elastic modulus from that of others.

Here, the step-wise (three-stage) bending motion of the elastic tube 1P (tubular member) as that described above is realized not only in increase of the internal pressure of tube A but in decrease (fall) of the pressure.

Next, a distinctive effect exhibited by this configuration will be described by using FIG. 14. FIG. 14(*a*) is a graph showing the relation between the elastic tube internal pressure and the curving angle when the bending portion 31 configured to have a single outer peripheral elastic tube which is shown in FIG. 11 is used, and FIG. 14(*b*) is a graph showing the relation between the elastic tube internal pressure and the curving angle when the bending portion 31*b* configured to have the triple outer peripheral elastic tube which is shown in FIG. 12 is used.

Figure 14:
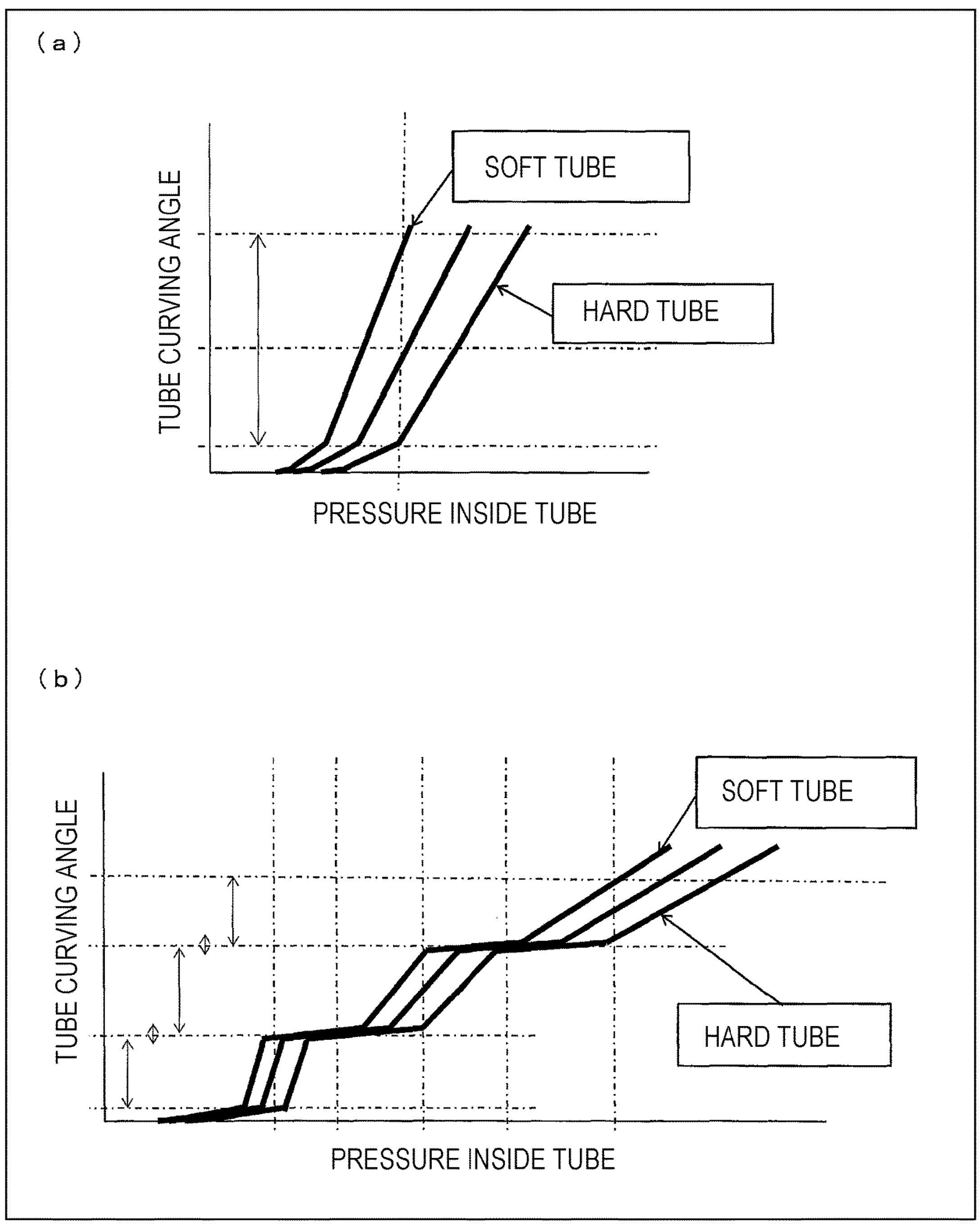
FIG. 14 is a graph showing the relation between the elastic tube internal pressure and the curving angle of the articulated bending portion according to Embodiment 3 of the present invention and is a graph showing the case of different bending characteristics of the elastic tubes.

In the case of the single outer peripheral elastic tube, variation in curving angles may be produced depending on bending parts due to variation in bending motion characteristics of the elastic tube, which is caused by influence of the elastic modulus, the wall thickness, the self-weight, and the like of the elastic tube, as shown in FIG. 14(*a*).

On the other hand, in the case of the triple outer peripheral elastic tube, even if the above-mentioned variation in bending motion characteristics is produced, the above-mentioned variation in curving angles can be retained in variation within one bending step at most, as shown in FIG. 14(*b*). For example, in the case of the triple, variation can be reduced to be approximately one-third. Further, if the pressurization state is controlled to be in the state exhibiting smaller variation with respect to pressurization fluctuation, that is, the pressurization state of a step for further suppressing inflation (a region with smaller inclination in FIG. 14(*b*)), such distinctive effect can be obtained that a highly-accurate curving angle can be retained.

This is especially effective in the case of a movable mechanism that operates by coordinating a pair of bending portions 31 in combination which is shown in FIG. 9 of Embodiment 2. That is, bending angles of a pair of bending portions 31 can be set to be highly accurately accorded with each other and a distal end portion can be moved while highly accurately maintaining the direction of the distal end portion constant. This provides a distinctive effect of yielding an image very easy for the operator to see especially when the distal end portion is equipped with a camera because the field of view can be moved without changing the angle of view.

Additionally, due to the presence of the elastic tubes 1*k*, 1*m*, and 1*n* on the outer periphery, such distinctive effect can be obtained that inflation in the elastic tube circumferential direction (the lateral direction), which does not contribute to bending, is suppressed and bending caused by inflation in the long-axis direction (the vertical direction), which directly affects the control of the curving angle, is effectively created. Further, since unnecessary inflation in the elastic tube circumferential direction is suppressed, degradation of the elastic tubes 1*a* to 1*d* caused by mechanical stress that occurs from repeated inflations and deflations can be prevented as well.

Embodiment 4

Yet another embodiment of the present invention will be described below based on FIGS. 15 and 16. For the sake of description, components having the same functionality as ones described in the previous embodiments are denoted with the same reference characters and description of such components is omitted.

Embodiment 3 described the configuration using three cylindrically-shaped elastic tubes whose inner circumferential surfaces and outer circumferential surfaces are even as outer peripheral elastic tubes. Embodiment 4 will describe an example in which an elastic tube having a different shape from that of the above-mentioned three elastic tubes is used as at least one of outer peripheral elastic tubes.

(Overview of the Articulated Bending Portion)

Figure 15:
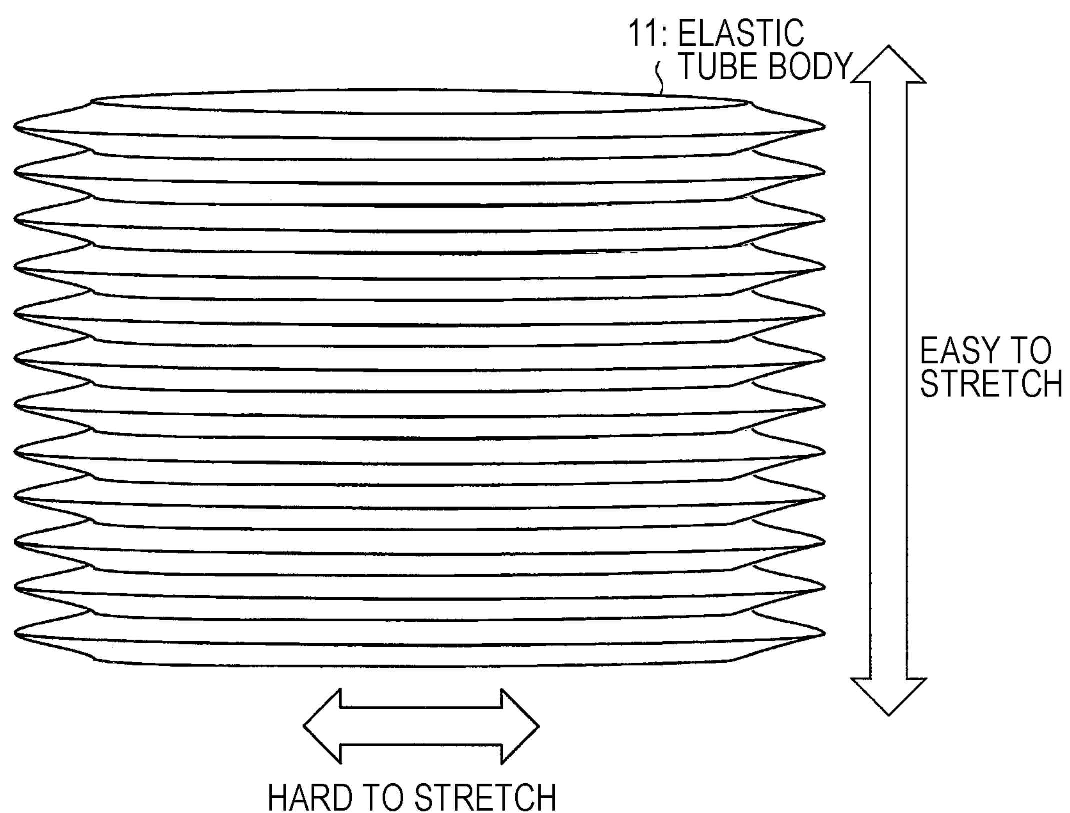
FIG. 15 is a perspective view showing a modification of an outer peripheral tube used for the articulated bending portion according to Embodiment 4 of the present invention.

FIG. 15 shows an example using an elastic tube having a bellows structure, as an outer peripheral tube.

Detailed description of the configuration of a bending portion 31*a* is omitted as it has been already described in Embodiments 1 and 2.

Embodiments 1 and 2 provided the description that the presence of the elastic tube on the outer periphery can provide such distinctive effect that inflation in the elastic tube circumferential direction (the lateral direction), which does not contribute to bending, is suppressed and bending caused by inflation in the long-axis direction (the vertical direction), which directly affects the control of the curving angle, is effectively created. Further, Embodiments 1 and 2 provided the description that since unnecessary inflation in the elastic tube circumferential direction is suppressed, degradation of the elastic tubes 1*a* to 1*d* caused by mechanical stress that occurs from repeated inflations and deflations can be prevented as well.

Further, Embodiment 3 described the example of the configuration including a plurality of outer peripheral elastic tubes. In order to enhance the advantageous effect obtained by this configuration including a plurality of outer peripheral elastic tubes, at least one of a plurality of outer peripheral elastic tubes may be changed to an anisotropically-stretchable elastic body. Here, the anisotropically-stretchable elastic body represents an elastic body whose stretchability in the long-axis direction thereof and stretchability in the short-axis direction thereof are different from each other. For example, a part of a plurality of outer peripheral elastic tubes may be set to have the bellows structure as shown in FIG. 15. Such structure can further suppress inflation in the elastic tube circumferential direction (the lateral direction), which does not contribute to bending, and further effectively create bending caused by inflation in the long-axis direction (the vertical direction), which directly affects the control of the curving angle.

Further, in the case of inflation in the elastic tube circumferential direction (the lateral direction), the wall thickness is decreased due to the stretch and the tension is further lowered. Therefore, only one side which first starts inflation may further inflate to largely bend, causing further variation in curving angles depending on bending portions. Against this case as well, at least one of a plurality of outer peripheral elastic tubes is changed into an anisotropically-stretchable elastic body, being able to largely improve the variation.

Further, for the use for minimally invasive surgery, the outer diameter of the articulated bending portion 30 is preferably smaller. In the configuration example of Embodiment 3, hollow portions are required to be provided among the outer peripheral elastic tubes so as to perform step-wise inflation suppression of the elastic tubes 1*a* to 1*d*, increasing the outer diameter.

Figure 16:
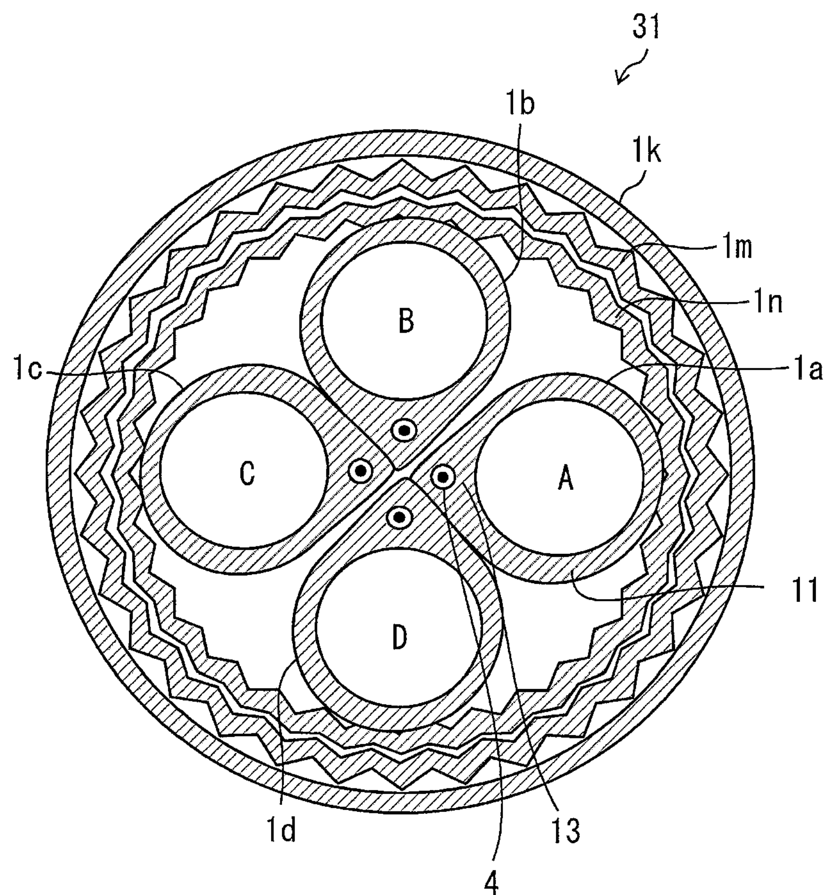
FIG. 16 is a cross-sectional view showing another modification of an outer peripheral tube used for the articulated bending portion according to Embodiment 4 of the present invention.

In order to suppress the above-mentioned increase in the outer diameter, the outer peripheral elastic tubes 1*m* and 1*n* are formed to have cross sections having the wave shape structure, as shown in FIG. 16, so that tension is hardly applied until this wave shape becomes to be flat due to inflation of the outer peripheral elastic tubes 1*m* and 1*n*. Accordingly, an advantageous effect equivalent to the case of provision of hollow portions can be obtained and regions for the hollow portions are reduced to be able to decrease the outer diameter of the articulated bending portion 30.

The above-described bellows structure and wave shape structure may be simultaneously incorporated in one outer peripheral elastic tube or may be respectively incorporated in separate outer peripheral elastic tubes to be used in combination. That is, the arbitrary configuration may be employed so as to optimize the bending motion characteristics of respective bending portions 31.

In the case where washing easiness is required, only the elastic tube 1*k* positioned outermost may be formed to be an elastic tube having no unevenness on the surface thereof as shown in FIG. 16 and stretchability thereof may be enhanced by using a material having higher elastic modulus so as not to generate problems in inflation of the elastic tubes 1*a* to 1*d*.

As described above, by using an elastic tube having the bellows structure and/or the wave shape structure for at least one of outer peripheral elastic tubes, the articulated bending portion 30 having a small diameter, high bendability, and small variation in curving angles of respective bending portions can be obtained.

Embodiment 5

Yet another embodiment of the present invention will be described below based on FIG. 17. For the sake of description, components having the same functionality as ones described in the previous embodiments are denoted with the same reference characters and description of such components is omitted.

Embodiment 4 described the configuration in which the bellows structure or the wave shape structure is used for at least one of outer peripheral elastic tubes, while Embodiment 5 will describe an example in which a mesh-like elastic body 12 is used instead of the outer peripheral elastic tube.

(Overview of the Articulated Bending Portion)

Embodiment 4 provided the description that the configuration of the outer peripheral elastic tube having the bellows structure or the wave shape structure can suppress inflation in the elastic tube circumferential direction (the lateral direction), which does not contribute to bending, and effectively create bending caused by inflation in the long-axis direction (the vertical direction), which directly affects the control of the curving angle. Embodiment 4 further provided the description that since unnecessary inflation in the elastic tube circumferential direction is suppressed, degradation of the elastic tubes 1*a* to 1*d* caused by mechanical stress that occurs from repeated inflations and deflations can be prevented as well and the articulated bending portion 30 having a small diameter can be obtained.

A part of a plurality of outer peripheral elastic tubes does not necessarily have the sealed tubular structure to obtain the aforementioned effect and the structure is not especially limited as long as the structure has the equivalent function.

Figure 17:
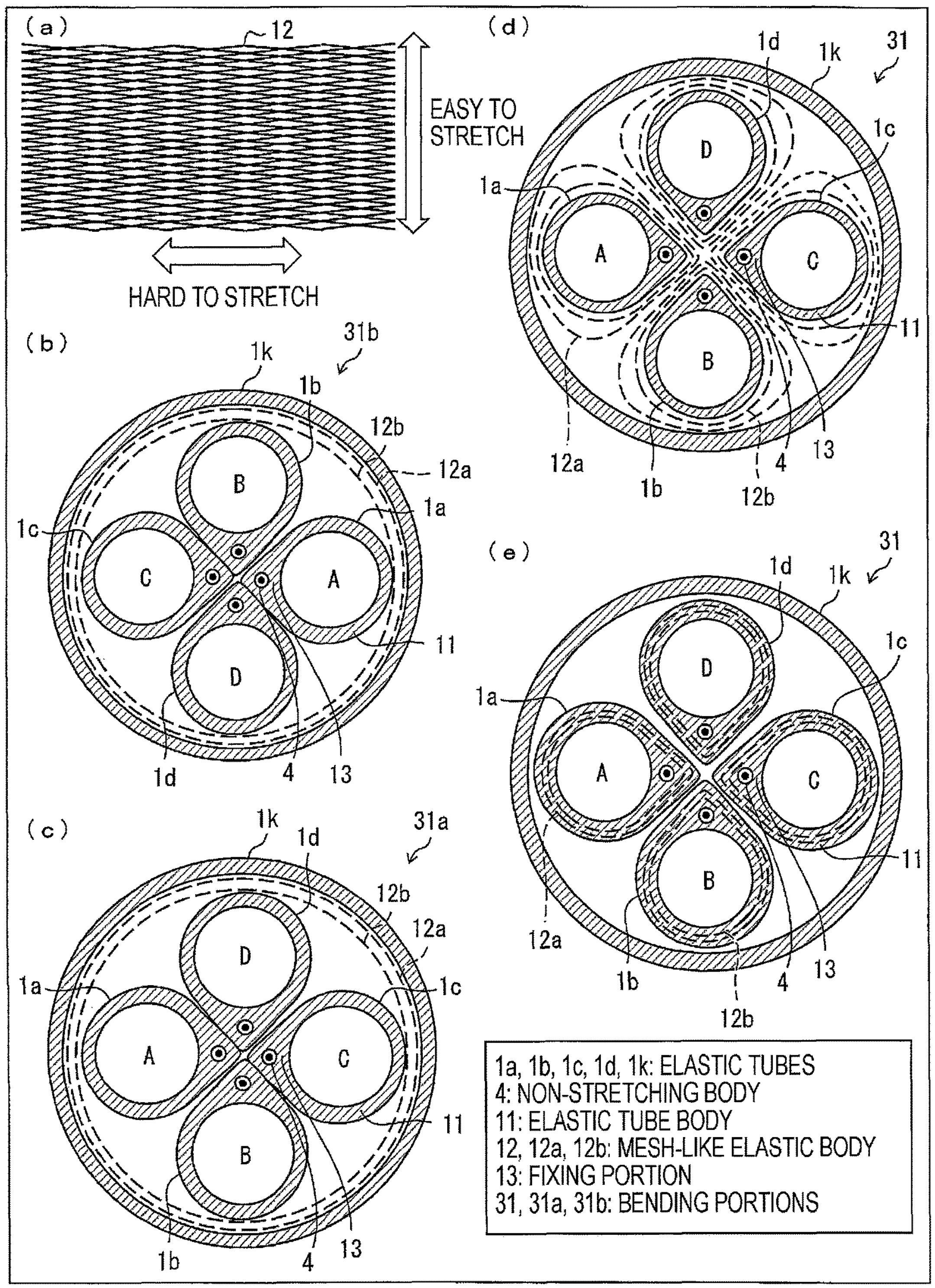
FIG. 17 is a plan development view of an elastic body having a mesh structure according to Embodiment 5 of the present invention and a cross-sectional view of the articulated bending portion in which the elastic body having the mesh structure is used.

An example of the mesh-like elastic body 12 which is used instead of the outer peripheral elastic tube is shown in FIG. 17 as an example. FIG. 17(*a*) is a plan development view of a sheet formed from the mesh-like elastic body 12 (referred to below as the "mesh sheet 12") and FIG. 17(*b*) is a cross-sectional view of the structure in which two layers of mesh sheets 12 are disposed inside the outermost peripheral elastic tube in a tubular shape.

When the mesh-like elastic body 12 constituting the mesh sheet 12 has crossings making rhomboidal shapes as shown in FIG. 17(*a*), the mesh sheet 12 in FIG. 17(*a*) easily stretches in the vertical direction but it is relatively hard for the mesh sheet 12 to stretch in the lateral direction. Thus, directionality can be provided to stretchability of the mesh sheet 12. Further, the mesh sheet 12 having arbitrary stretchability can be formed by changing the elastic modulus of a material used for the mesh-like elastic body 12 or changing the size or the crossing angle of meshes.

By employing such configuration in which a plurality of mesh sheets 12, which has different stretchabilities between the vertical direction and the lateral direction, are arranged in the tubular shape inside the outermost peripheral elastic tube as shown in FIG. 17(*b*), inflation in the elastic tube circumferential direction (the lateral direction), which does not contribute to bending, is suppressed and bending caused by inflation in the long-axis direction (the vertical direction), which directly affects the control of the curving angle, is effectively created. In the example shown in FIG. 17(*b*), the bending portion 31 has a triple layer structure composed of one elastic tube 1*k* and two mesh-like elastic bodies 12*a* and 12*b* on the cross section thereof.

Here, this advantageous effect is not limitedly exhibited to the case where a plurality of outer peripheral elastic tubes are arranged in the nested fashion, but this effect can be obtained even in the case of a use in a single outer peripheral elastic tube as well.

Further, in the case of inflation in the elastic tube circumferential direction (the lateral direction), the wall thickness is decreased due to the stretch and the tension is further lowered. Therefore, only one side which first starts inflation may further inflate to largely bend, causing further variation in curving angles depending on bending portions. Against this case as well, the mesh sheet 12 which has different stretchabilities between the vertical direction and the lateral direction is used instead of a part of outer peripheral elastic tubes, being able to largely improve the variation.

Further, for the use for minimally invasive surgery, the outer diameter of the articulated bending portion 30 is preferably smaller. In the configuration example of Embodiment 3, hollow portions are required to be provided among the outer peripheral elastic tubes so as to perform step-wise inflation suppression of the elastic tubes 1*a* to 1*d*, increasing the outer diameter. In order to suppress the above-mentioned increase in the outer diameter, such configuration is employed that the mesh sheet 12 is disposed inside the outermost peripheral elastic tube 1*k* in the tubular shape as shown in FIG. 17(*b*) so that tension is hardly applied until this mesh sheet 12 extends to some extent. Accordingly, an advantageous effect equivalent to the case of provision of hollow portions can be obtained and regions for the hollow portions are almost eliminated, being able to further decrease the outer diameter of the articulated bending portion 30.

Although not shown, such configuration may be employed that the mesh sheet 12 formed in a tubular shape is embedded in a thick wall portion of the outermost peripheral elastic tube 1*k*. Even this configuration enables the outermost peripheral elastic tube 1*k* in the bending portion 31 to bend stepwise.

Further, such configuration may be employed that two layers of mesh sheets 12 are wrapped around the outer circumferential surfaces of the elastic tubes 1*a* to 1*d* as shown in FIG. 17(*d*). Accordingly, the elastic tubes 1*a* to 1*d* have a multi-layer structure on shapes of cross sections thereof orthogonal to the axis direction, so that inflation in the circumferential direction (the lateral direction) of the elastic tubes 1*a* to 1*d*, which does not contribute to bending, is suppressed and bending caused by inflation in the long-axis direction (the vertical direction), which directly affects the control of the curving angle, can be effectively created.

Further, this configuration can reduce interference by other elastic tubes with respect to a bending motion of a specific elastic tube. Additionally, a moderate allowance with respect to inflation can be provided as well by using a gap between each elastic tube and the mesh sheet 12 and a gap between the mesh sheets 12 without increasing the outer diameter of the outermost peripheral elastic tube 1*k*. Therefore, the bending motion can be controlled with high accuracy. Further, the presence of the above-mentioned moderate allowance increases the freedom in design of the elastic tubes 1*a* to 1*d*.

Further, as shown in FIG. 17(*e*), such configuration may be employed that a plurality of mesh sheets 12*a* to 12*d* having different stretch characteristics from each other are embedded inside (between the inner circumferential surface and the outer circumferential surface of) each of the elastic tubes 1*a* to 1*d* to be integrated.

By the employment of the above-mentioned configuration, step-wise stretch characteristics can be provided to the elastic tubes 1*a* to 1*d* themselves and the diameter of the articulated bending portion 30 can be reduced more than the configuration shown in FIG. 17(*d*). Further, hysteresis characteristics of the elastic tubes 1*a* to 1*d* are lowered so as to be able to improve controllability of bending of the bending portion 31.

Here, the stretch characteristics chiefly represent an inherent property related to inflation and deflation of an elastic tube or the like which is defined based on the elastic modulus of a material used for the elastic tube and the size and the crossing angle of meshes of a mesh-like elastic body (easiness and difficulty in extension).

In the case where washing easiness is required, only the outermost peripheral elastic tube 1*k* may be formed to be an elastic tube having no unevenness on the surface thereof as shown in FIG. 17(*b*) and stretchability thereof may be enhanced by using a material having higher elastic modulus so as not to generate problems in inflation of the elastic tubes 1*a* to 1*d*.

As described above, with the use of the outer peripheral elastic tube having the inner circumferential surface on which the mesh-like elastic bodies 12 (mesh sheet 12) are disposed, the articulated bending portion 30 having a smaller diameter, higher bendability, and smaller variation in curving angles of respective bending portions can be obtained.

Embodiment 6

Yet another embodiment of the present invention will be described below based on FIGS. 17 to 19. For the sake of description, components having the same functionality as ones described in the previous embodiments are denoted with the same reference characters and description of such components is omitted.

Embodiment 5 described the example in which the mesh sheets 12 are disposed inside the outer peripheral elastic tube in a tubular shape, while Embodiment 6 will describe an example in which a single outer peripheral elastic tube 1*k* which is the simplest configuration is used for controlling middle and proximal end portions and the configuration of Embodiment 5 is used for a distal end portion.

(Overview of the Articulated Bending Portion)

Figure 18:
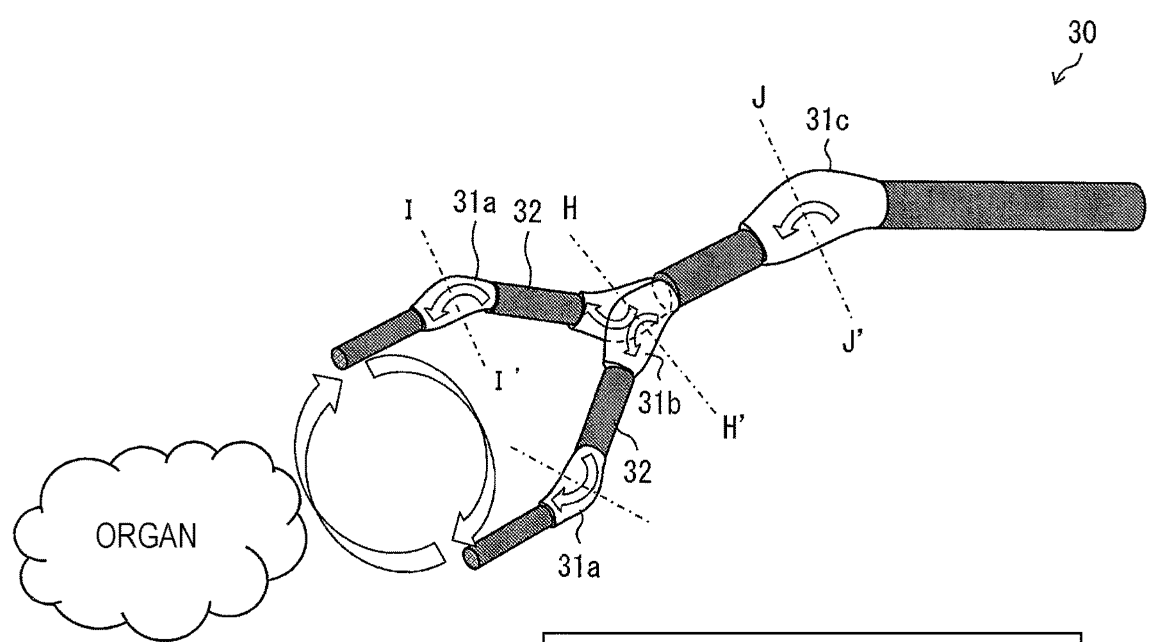
FIG. 18 is a perspective view showing the bending motion of the articulated bending portion according to Embodiment 6 of the present invention.

As shown in FIG. 18, an example of such configuration is shown that the movable mechanism which operates with two bending portions 31*a* and 31*b* in combination and described in Embodiments 2 and 5 is used for the distal end portion having a camera attached thereon and a bending portion 31*c* using a single outer peripheral elastic tube 1*k* is used for controlling the middle and proximal end portions.

Detailed description of the configuration of the bending portions 31*a* and 31*b* on the distal end portion side is omitted as the configuration has been already described in Embodiments 2 and 5. A cross-sectional view of the bending portion 31*a* is shown in FIG. 17(*c*) and a cross-sectional view of the bending portion 31*b* is shown in FIG. 17(*b*).

Figure 19:
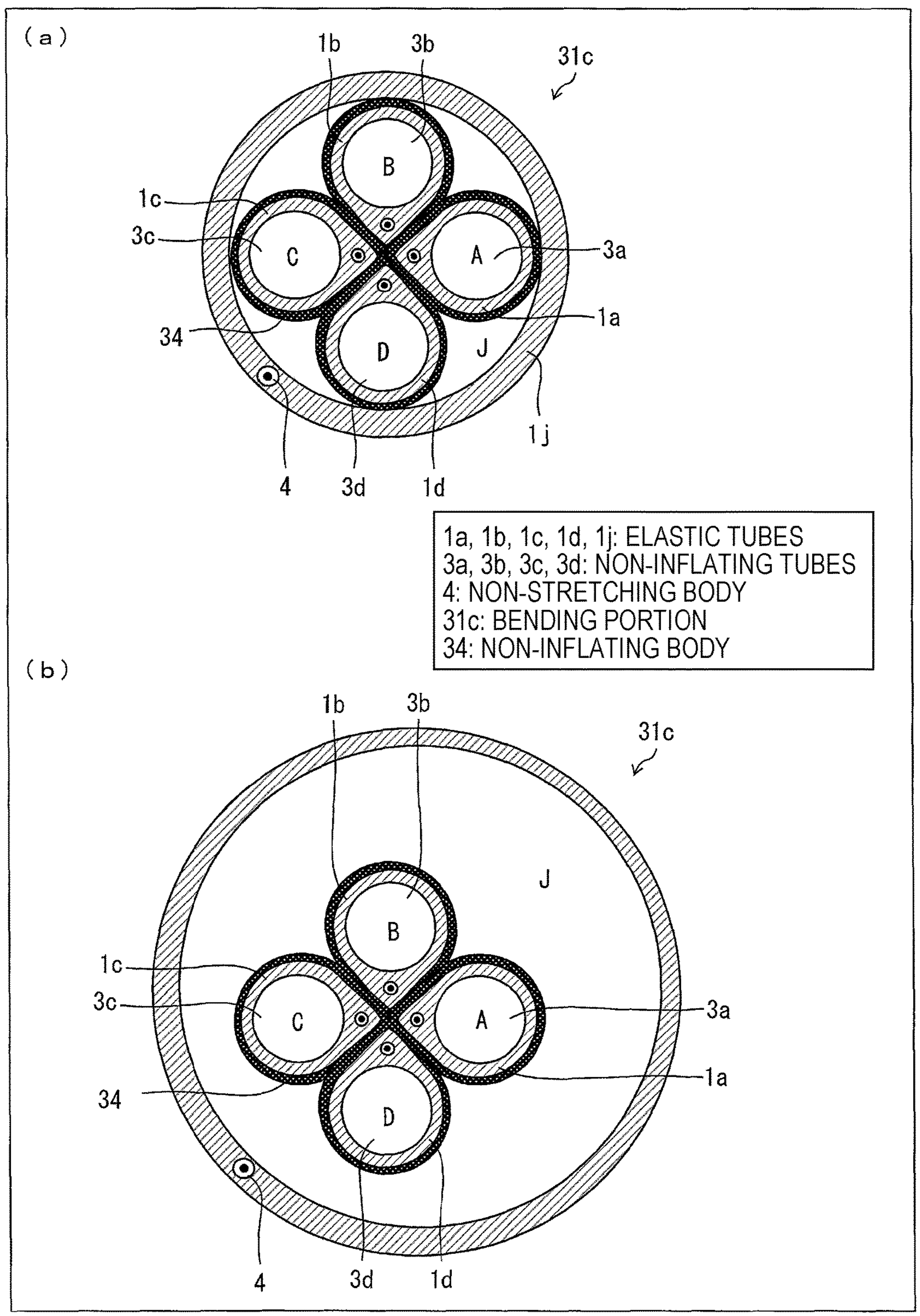
FIGS. 19(*a*) and 19(*b*) are cross-sectional views of the articulated bending portion according to Embodiment 6 of the present invention.

The cross-sectional structure of the bending portion 31*c* on the middle and proximal end side is shown in FIG. 19(*a*). An elastic tube 1*j* is used for controlling bending in the middle and proximal end portions, and the elastic tubes 1*a* to 1*d* for use in the distal end portion are disposed in the hollow portion of the elastic tube 1*j*. The elastic tube 1*j* has a structure in which the non-stretching body 4 is embedded between the inner circumferential surface and outer circumferential surface of the elastic tube 1*j*.

This configuration reduces burden on the bending motion of the elastic tube 1*j* caused by the elastic tubes 1*a* to 1*d*, so bending motion with better controllability can be achieved. The elastic tubes 1*a* to 1*d* for use in the distal end portion have a structure with the non-inflating body 34 wrapped around them. This allows the bending portions 31*a* and 31*b* to bend without causing the bending portion 31*c* to bend by pressurizing the elastic tubes 1*a* to 1*d*. For enhancing the non-inflatability, preventing interference with other tubes, and increasing the bend controllability, it is desirable that the non-inflating body 34 be wrapped around each of the elastic tubes 1*a* to 1*d* as shown in FIG. 19.

Further, as to bending of the elastic tube 1*j*, the foregoing description applies: a bending motion is produced by pressurizing and inflating the elastic tube 1*j* as shown in FIG. 19(*b*). For example, bending in a particular direction can be achieved by fixing the position of the non-stretching body 4 of the elastic tube 1*j* in a bending portion 31, or bending in a certain direction can be achieved by changing the position of the non-stretching body 4 in another bending portion. In this manner, bending motions such as avoiding a predetermined organ or going behind an organ and viewing it from the back side can be produced based on the position of the non-stretching body 4 embedded in the elastic tube in advance. Because of a simple structure, there are not many other tubes that can be burden, enabling stable bending motions.

An application of this structure to the distal end portion, at which a camera is attached, and the middle portion is shown in FIG. 18. An approximate direction of the camera distal end portion is determined by pressurizing the elastic tube 1*j* to bend the bending portion 31*c*, and the field of view is moved by bending the bending portions 31*a* and 31*b* provided on the distal end portion side in the inverse direction with the configuration described in Embodiment 5. As the mesh-like elastic bodies 12*a* and 12*b* (mesh sheets 12*a* and 12*b*) are disposed on the inner circumferential surface of the outer peripheral elastic tube 1*k*, the curving angles of the bending portions 31*a* and 31*b* can be accorded with each other with high accuracy. Further, as the angle of view stays unchanged, non-frustrating movement of the field of view can be achieved.

Further, according to the above-described configuration, the number of elastic tubes to be bundled is small, accordingly the cross-sectional shape of the articulated bending portion 30 is nearly circular, and thus unevenness of the surface is reduced. This makes the elastic tube 1*a* easy to wash and sterilize, facilitating its reuse.

Additionally, because the above-described configuration can dispose the non-stretching body 4 and the cable connected with the medical device further inside an elastic tube located within a hollow interior, they can be placed in locations protected by multiple layers of elastic tubes. Thus, if part of the non-stretching body 4 and the cable connected with the medical device is broken for some reason, the broken part is protected by multiple layers of elastic tubes, thus lowering the risk of damage to the human body. For example, if part of the non-stretching body 4 is broken for some reason, the risk of the broken part of the non-stretching body 4 damaging the human body is low even when the non-stretching body 4 has lower stretchability than the elastic tube 1*a*. As another example, if the cable connected with the medical device is an electric cable, adverse effects such as current leakage due to breakage of the electric cable can be avoided in the human body. Besides, since gas is injected in the elastic tube body 11, should the electric cable is broken, adverse effects of current leakage can be avoided in the elastic tube body 11 because electrical conductivity in the elastic tube body 11 is low.

Embodiment 7

Yet another embodiment of the present invention will be described below based on FIGS. 20 to 25. For the sake of description, components having the same functionality as ones described in the previous embodiments are denoted with the same reference characters and description of such components is omitted.

Embodiments 5 and 6 mainly described the examples of the bending portions 31*a* and 31*b*, which have the elastic tube 1*k* on the outermost periphery thereof, have the inner circumferential surfaces on which the mesh sheets 12 are disposed in a tubular shape, and have the elastic tubes 1*a* to 1*d* pressurized for producing a bending motion inside the mesh sheet 12 having the tubular shape, and the articulated bending portion 30 using the bending portions 31*a* and 31*b* as the bending portions of the distal end portion.

Embodiment 7 will describe an example in which in the articulated bending portion 30, which has the configuration that four elastic tubes are used for controlling middle and proximal end portions and an elastic tube for controlling a distal end portion is disposed in a hollow portion of each of the elastic tubes, the configurations of these elastic tubes are used and an example in which the distal end portion of Embodiment 6 is provided for this distal end.

(Overview of the Articulated Bending Portion)

Figure 20:
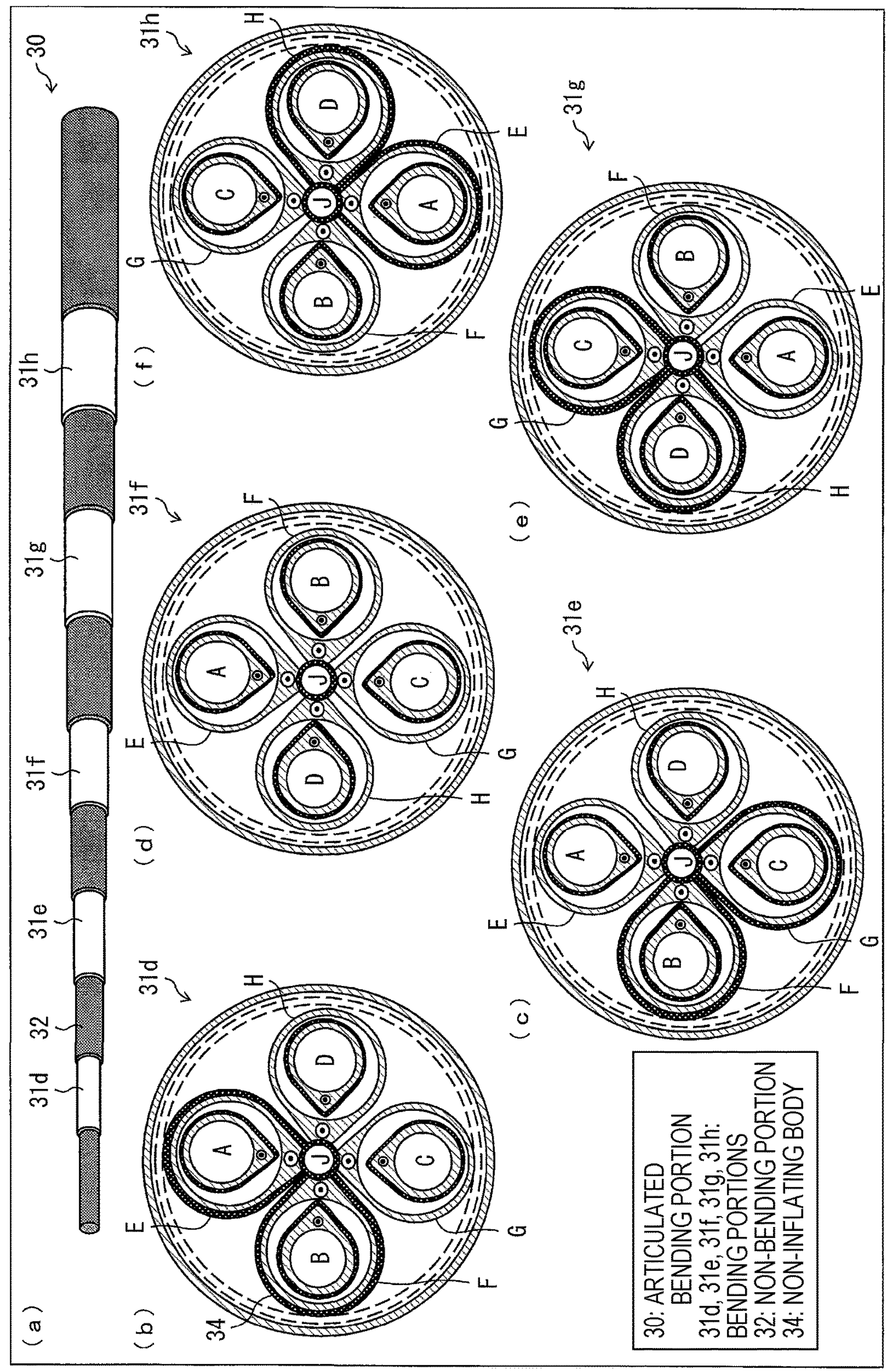
FIGS. 20(*a*) to 20(*f*) are perspective and cross-sectional views showing a specific example of the middle and proximal end portions of the articulated bending portion according to Embodiment 7 of the present invention.

FIG. 20 shows an example of the configuration of a movable mechanism having a bending portion in which four elastic tubes are used for controlling middle and proximal end portions on the assumption that the distal end portion to which a camera is attached is driven by two bending portions 31*a* and 31*b*, which have been described in Embodiment 6, in combination and a bending portion which produces a bending motion in a single direction is used for the middle portion.

Here, detailed description of the configurations of the bending portions 31*a*, 31*b*, and 31*c* on the distal end portion side is omitted as the configurations have been already described in Embodiment 6.

The cross-sectional structure of a bending portion 31*f* on the middle and proximal end portion side is described by taking an example of FIG. 20(*d*). Elastic tubes 1*e* to 1*h* (first elastic tubes) are used for controlling bending in the middle and proximal end portions, and elastic tubes 1*a* to 1*d* (second elastic tubes) used in the distal end portion are disposed in the hollow interiors of the elastic tubes 1*e* to 1*h* respectively. Further, a non-inflating tube 3*j* is disposed on the center of the bending portion 31*c* so as to control bending of the bending portion 31*c*.

This configuration reduces burden on the bending motion of the elastic tubes 1*e* to 1*h* caused by the elastic tubes 1*a* to 1*d*, so bending motions with better controllability can be achieved.

The elastic tubes 1*a* to 1*d* for use in the distal end portion are structured such that the non-inflating body 34 is wrapped around them. This allows the bending portions 31*a* and 31*b* to bend without causing the bending portion 31*f* to bend by pressurizing the elastic tubes 1*a* to 1*d*.

The non-inflating tube 3*j* may also have the same configuration. However, an inflation portion is composed of an outer peripheral elastic tube 1*j* as described later, so that an inflation portion is not required to be provided and therefore a tube composed only of the non-inflating body 34 is employed here.

For reduction in a diameter of the articulated bending portion 30 and enhancement of flexibility, it is preferable that the non-inflating tube 3*j* have a small diameter to be able to be disposed in a gap positioned on the center of the bending portion 31*c*.

Figure 25:
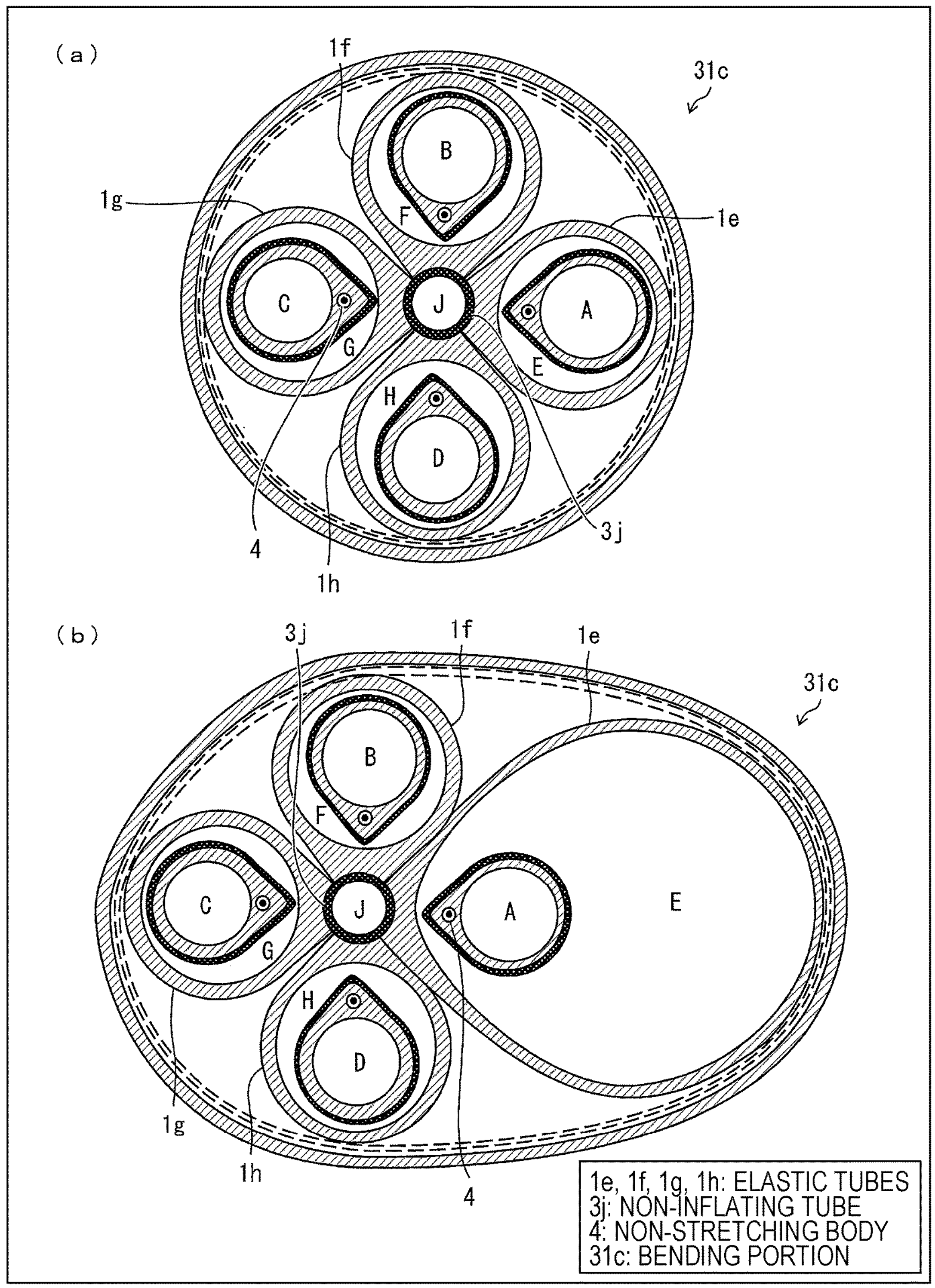
FIG. 25 is a cross-sectional view showing another example of the internal structure of the middle and proximal end portions of the articulated bending portion according to Embodiment 7 of the present invention.

Further, as shown in FIG. 25, the non-inflating tube 3*j* can be disposed on the center of the bending portion 31*c*, so that the non-inflating tube 3*j* can be bonded to the elastic tubes 1*e* to 1*h* (first elastic tubes) so as to be allowed to function as a non-stretching body of these four elastic tubes. In this case, the non-stretching body 4 is not required to be embedded in the elastic tubes 1*e* to 1*h* (first elastic tubes), thereby being able to reduce manufacturing cost.

Further, as to bending of the elastic tubes 1*e* to 1*h*, the foregoing description applies: a bending motion is produced by pressurizing and inflating the elastic tubes 1*e* to 1*h*. For example, bending in a particular direction can be achieved by pressurizing the elastic tube 1*e* in the bending portion 31, or bending in a certain direction can be achieved by changing the position of the elastic tube 1*e* in another bending portion. In this manner, bending motions such as avoiding a predetermined organ or going behind an organ and viewing it from the back side can be produced based on the positions of the elastic tubes incorporated in advance. Because of a simple structure, there are not many other tubes that can be burden, enabling stable bending motions.

Pressurizing portions may be provided at two or more locations, including a pressurizing portion for pressurizing four tubes A to D that drive bending portions in the distal end portion, a pressurizing portion for pressurizing the tube J that drives bending portions in the middle portion, and a pressurizing portion for pressurizing four tubes E to H that drive the bending portions in middle and proximal end portions. With this configuration, bending of the bending portions 31*a* and 31*b*, bending of the bending portion 31*c*, and bending of the bending portions 31*d* to 31*h* can be controlled in a mutually-independent manner.

A specific example of application of this structure to the middle and proximal end portions is shown in FIG. 20. FIG. 20(*a*) shows an exemplary configuration that uses four elastic tubes and has five bending portions 31*d* to 31*h*. FIG. 20(*a*) omits illustration of the distal end portion, and only tubes A to D, used in the distal end portion, are shown in the cross-sectional views shown in FIGS. 20(*b*) to 20(*f*). Detailed description of the configuration of the distal end portion is omitted as it has been already described in Embodiment 6.

The cross sections of the bending portions 31 are structured as shown in FIGS. 20(*b*), 20(*c*), 20(*d*), 20(*e*), and 20(*f*) in order from the side closer to the distal end portion. They will be referred to as a first bending portion 31*d*, a second bending portion 31*e*, a third bending portion 31*f*, a fourth bending portion 31*g*, and a fifth bending portion 31*h* in sequence.

As shown in FIG. 20(*b*), the first bending portion 31*d* has a structure in which tubes E and F are wrapped with the non-inflating body 34, being configured so as not to inflate, or not bend, when being pressurized.

Similarly, the second bending portion 31*e* in FIG. 20(*c*) has a structure in which tubes F and G are wrapped with the non-inflating body 34, the third bending portion 31*f* in FIG. 20(*d*) has a structure in which none of the tubes F to H is wrapped with the non-inflating body 34, the fourth bending portion 31*g* in FIG. 20(*e*) has a structure in which tubes G and H are wrapped with the non-inflating body 34, and the fifth bending portion 31*h* in FIG. 20(*f*) has a structure in which tubes E and H are wrapped with the non-inflating body 34.

In addition, the positions of some of the tubes are interchanged in non-bending portions 32; in the illustrated configuration, none of the tubes are interchanged in the non-bending portion 32 between FIGS. 20(*b*) and 20(*c*), whereas tube F and tube H are interchanged in the non-bending portion 32 between FIGS. 20(*c*) and 20(*d*), tube E and tube G are interchanged in the non-bending portion 32 between FIGS. 20(*d*) and 20(*e*), and tube F and tube H are interchanged again in the non-bending portion 32 between FIGS. 20(*e*) and 20(*f*).

Bending motions in the middle and proximal end portions are produced by pressurizing and inflating the tubes E to H. By adopting such a configuration, the position movement feature for avoidance joints shown in FIG. 21 and the interval varying feature for avoidance joints shown FIG. 22 can be provided.

These features will be described in greater detail using drawings. First, FIG. 21(*b*) shows a bending state during pressurization. As tube E has a structure in which it is wrapped with the non-inflating body 34 in the first and fifth bending portion 31*d*, 31*h*, it does not bend when pressurized. Also, because the position of tube E is interchanged in the non-bending portion 32 between the third bending portion 31*f* and the fourth bending portion 31*g*, bends in opposite directions occur across that non-bending portion 32. That is, the bending state shown in FIG. 21(*b*) is assumed.

Figure 21:
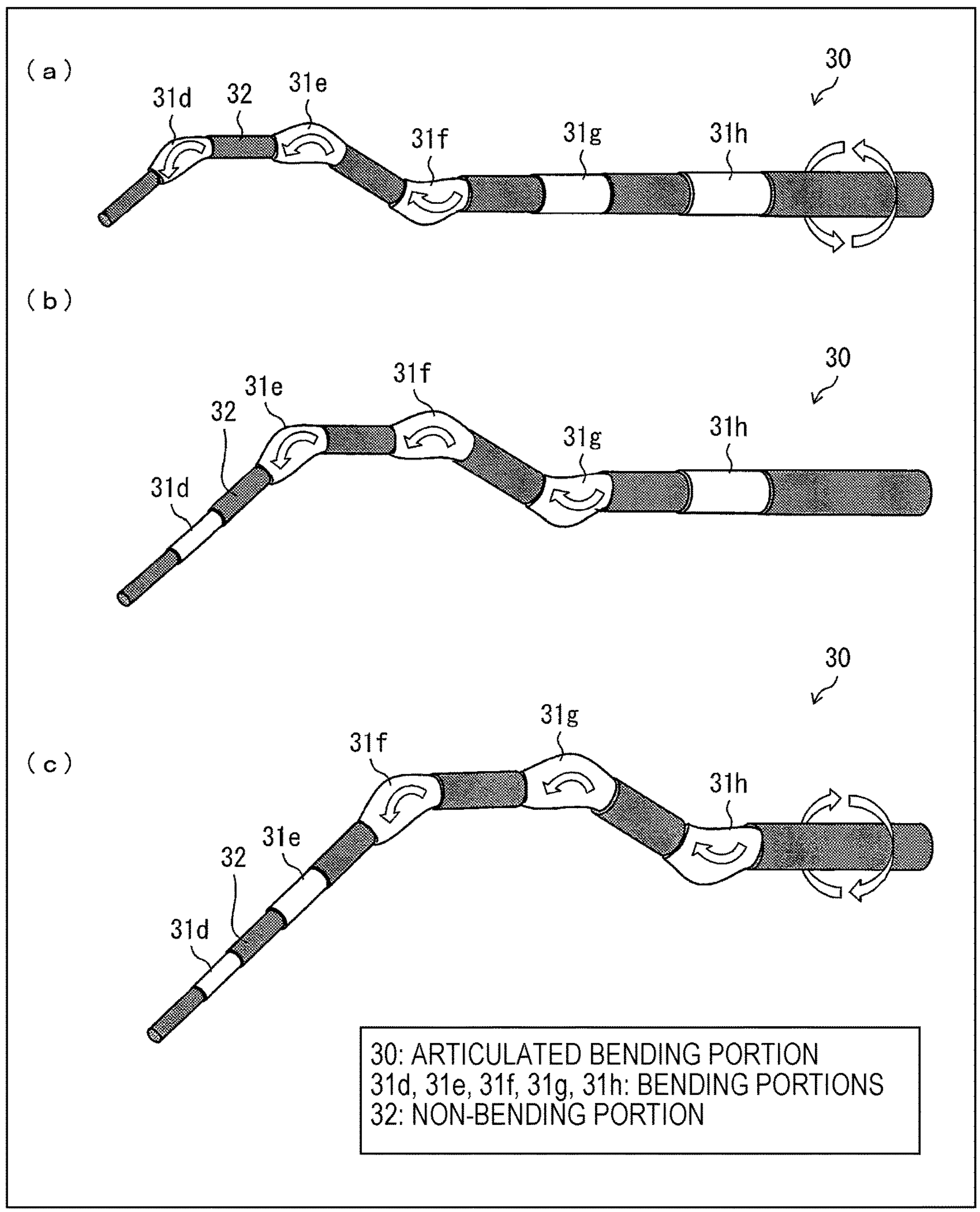
FIG. 21 is a perspective view showing an example of bending motion in the middle and proximal end portions of the articulated bending portion according to Embodiment 7 of the present invention.
Figure 22:
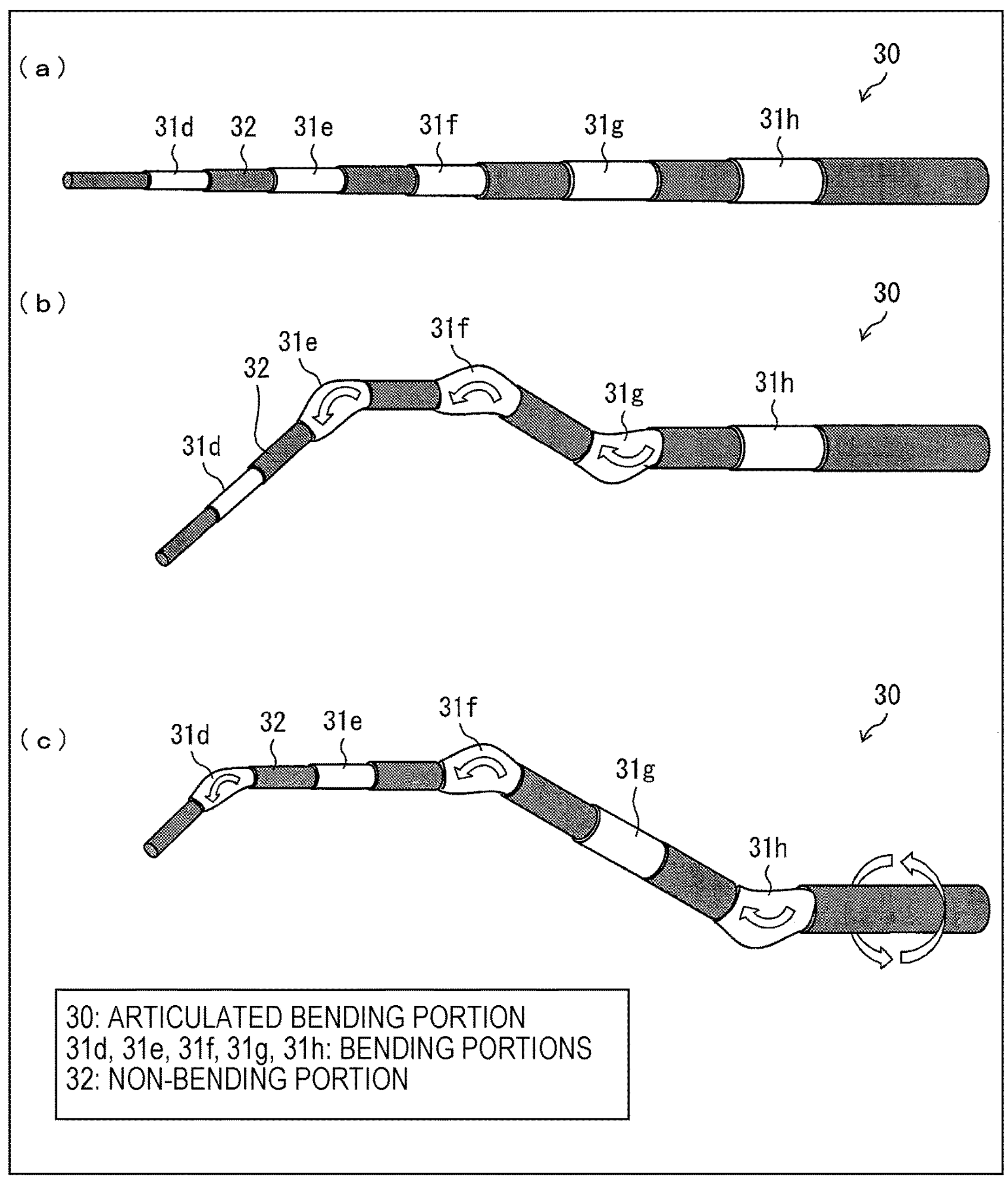
FIG. 22 is a perspective view showing another example of bending motion in the middle and proximal end portions of the articulated bending portion according to Embodiment 7 of the present invention.

Bending motions can be produced in the other three tubes with the same principle: the state in FIG. 21(*a*) occurs when tube H is pressurized, the state in FIG. 21(*c*) occurs when tube F is pressurized, and the state in FIG. 22(*c*) occurs when tube G is pressurized.

Next, a case is described where a bend is to be made in a portion closer to the distal end side as shown in FIG. 21(*a*) from the state of FIG. 21(*b*). In this case, tube E is gradually depressurized and tube H is gradually pressurized instead. At the same time, the entire tube of the articulated bending portion 30 is rotated by 90 degrees. For the cross-sectional structure in FIG. 20, counterclockwise rotation is gradually applied so that tube H moves to the position of tube E. By doing so, smooth transition from the state of FIG. 21(*b*) to the state of FIG. 21(*a*) can be achieved.

Likewise, for a bent to occur on the proximal end side conversely, tube E is gradually depressurized and tube F is gradually pressurized instead, and at the same time, the entire tube is rotated 90 degrees clockwise.

As shown in FIG. 22, when the range of joint bending is to be widened from the state of FIG. 22(*b*) to the state of FIG. 22(*c*) in order to increase the distance of avoidance, tube E may be gradually depressurized and tube G may be gradually pressurized instead, and at the same time the entire tube may be rotated 180 degrees.

The bending motions shown above are only a few examples and a wide variety of bending motions can be produced by appropriately setting the pressurization states of the four elastic tubes and rotation of the entire tube of the articulated bending portion 30.

(Primary Component Structure of the Articulated Bending Portion)

Connection between the articulated bending portion on the distal end portion side described in Embodiment 6 and the articulated bending portion on the proximal end portion side described in Embodiment 7 will now be described in further detail by using FIGS. 23 and 24.

Figure 23:
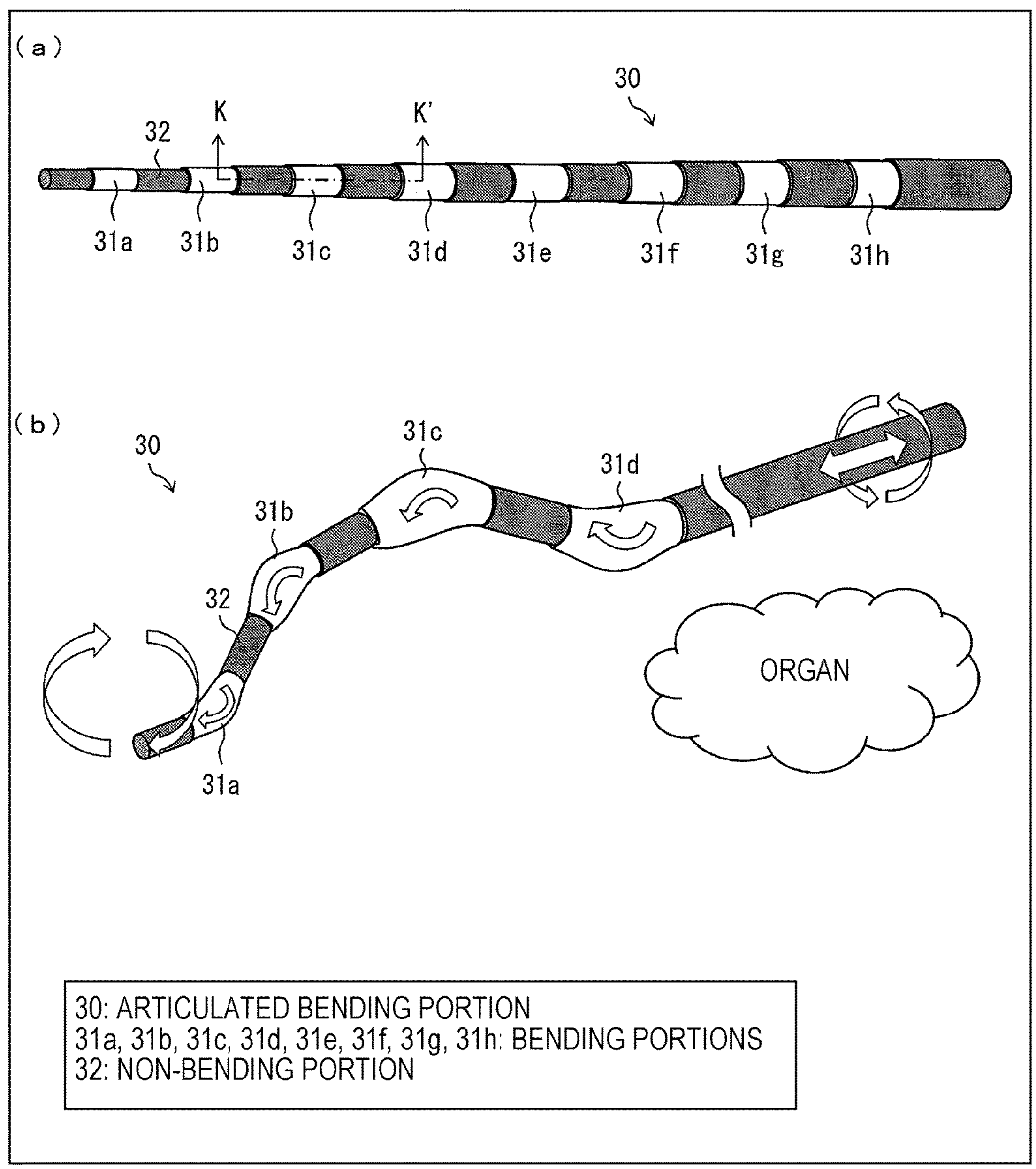
FIG. 23 is a perspective view showing a specific example of the configuration of the articulated bending device according to Embodiment 7 of the present invention.

FIG. 23 is a perspective view showing the articulated bending portion 30 formed by connecting the articulated bending portion on the distal end portion side shown in FIG. 18 and the articulated bending portion on the proximal end portion side shown in FIGS. 20 to 22 with each other. For the sake of description, components having the same functionality as ones described in the previous embodiments are denoted with the same reference characters and description of such components is omitted.

FIG. 23(*a*) shows a state that the articulated bending portion 30 is not bent, and FIG. 23(*b*) shows a bending motion of the articulated bending portion 30. Further, FIG. 24(*a*) is a cross-sectional view of a portion at the bending portions 31*b* to 31*d* in the articulated bending portion 30 shown in FIG. 23(*a*), FIG. 24(*b*) is a cross-sectional view of the bending portion 31*b* in FIG. 24(*a*), FIG. 24(*c*) is a cross-sectional view of the non-bending portion 32 positioned between the bending portions 31*b* and 31*c* shown in FIG. 24(*a*), FIG. 24(*d*) is a cross-sectional view of the bending portion 31*c* shown in FIG. 24(*a*), FIG. 24(*e*) is a cross-sectional view of the non-bending portion 32 positioned between the bending portions 31*c* and 31*d* in FIG. 24(*a*), and FIG. 24(*f*) is a cross-sectional view of the bending portion 31*d* shown in FIG. 24(*a*).

Figure 24:
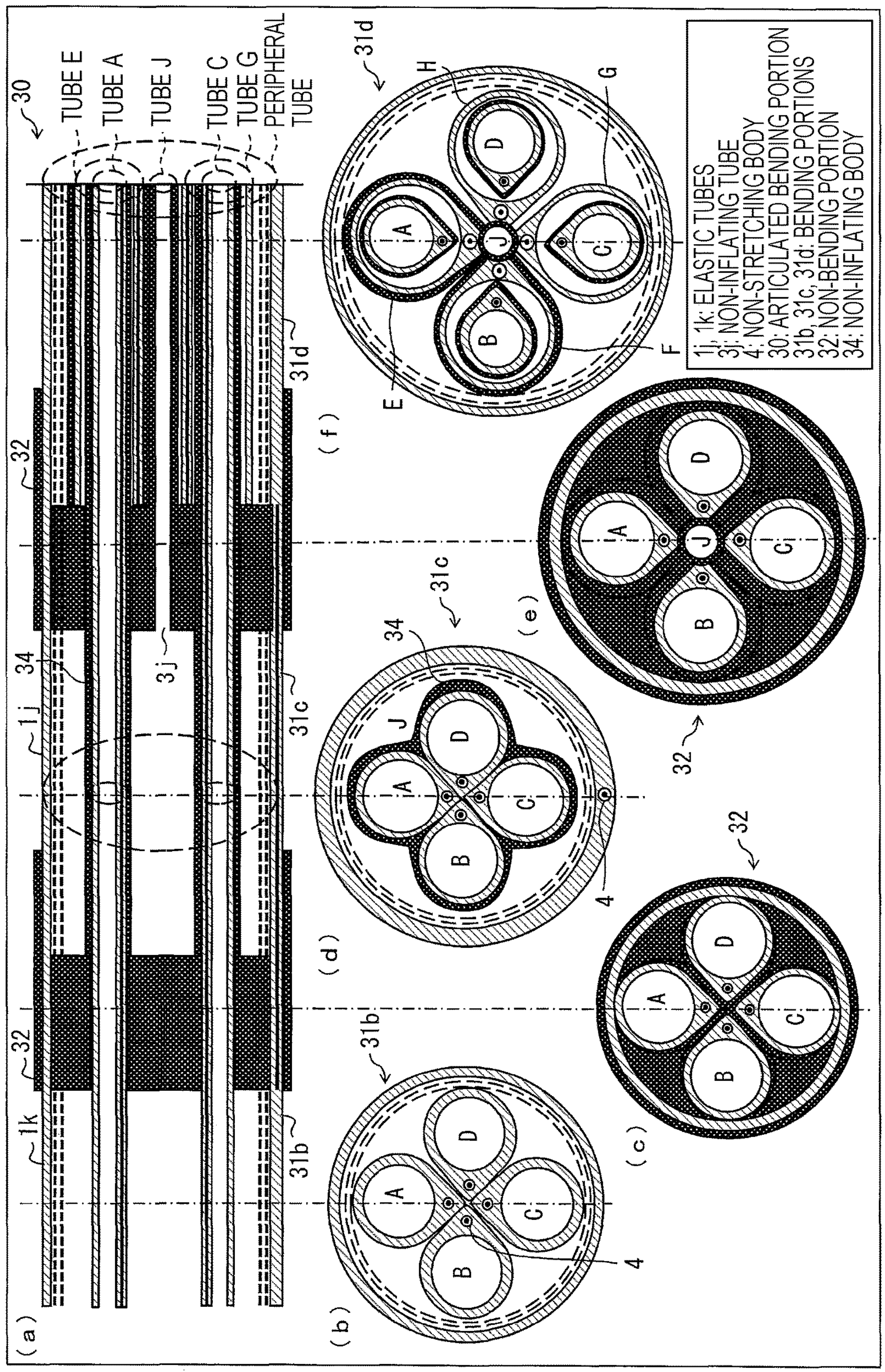
FIGS. 24(*a*) to 24(*f*) are cross-sectional views showing a specific example of a primary component structure of the articulated bending portion according to Embodiment 7 of the present invention.

As shown in FIG. 24(*a*), tubes A to D continue from the distal end portion side to the proximal end portion side. Further, the non-inflating body 34 is wrapped around the circumference in areas other than the bending portions 31*a* and 31*b* and thus, inflation is not produced even if pressurization is applied. Further, the non-stretching body for efficiently producing bending is embedded in the vicinity of the center of the bending portion, in each of the tubes.

Further, tube J communicates with the elastic tube 1*j* positioned on the outermost periphery in the bending portion 31*c* and the elastic tube 1*j* is sealed by the non-bending portions 32 positioned on the both sides thereof. Here, the mesh-like elastic bodies 12 are disposed on the inner circumferential surface of the elastic tube 1*j* positioned on the outermost periphery, so that internal pressure is directly applied to the elastic tube 1*j* positioned on the outermost periphery. Further, the non-stretching body 4 for efficiently producing bending is embedded on the bottom side of the bending portion 31*c* in FIG. 24(*d*). Accordingly, when tube J is pressurized, bending is produced so that the distal end portion is directed down.

Tubes E to H have already been described in detail above. FIG. 24(*f*) is the same figure as FIG. 20(*b*). Here, tubes E to H are sealed at end portions of respective tubes as shown in FIG. 24(*e*). Further, two-layered mesh-like elastic bodies 12 having a tubular shape are disposed inside the outer peripheral elastic tube 1*k*.

Description was provided with illustration of FIG. 24(*a*) on the assumption that the tube diameter of the articulated bending portion 30 is constant, for the sake of description. However, the number of tubes is lowered and gaps are increased toward the distal end portion side, so that it is preferable to reduce the diameter toward the distal end as shown in FIGS. 23 and 24(*b*) to 24(*f*). Accordingly, a burden on a bending motion caused by the self-weight can be reduced on each bending portion.

In the case where the articulated bending portion 30 according to this embodiment is used in an endoscopic camera, after the whole of the articulated bending portion 30 is first positioned while avoiding an organ by the configuration shown in FIGS. 20 to 22, an approximate direction of the camera distal end portion is determined by the bending portion 31*c* shown in FIG. 18. Then, an operation can be conducted while finely adjusting the field of view by manipulating the bending portions 31*a* and 31*b*, and thus non-frustrating movement of the field of view for an operator can be achieved.

Such complicated movements can be achieved with a simple structure involving only pressurization of the nine elastic tubes and rotation of the entire tube and a mechanism for attachment and removal, providing an extended range of application to relatively complicated surgeries.

Embodiment 8

Yet another embodiment of the present invention will be described below. For the sake of description, components having the same functionality as ones described in the previous embodiments are denoted with the same reference characters and description of such components is omitted.

(Applications of Medical Devices)

In a case where a catheter as a medical device is attached to the mounting portion at the distal end of the endoscope part 10, a cord for feeding air to the catheter can double as the non-stretching body 4. Air fed to the catheter causes a balloon of the catheter to inflate.

The catheter may be of a guide wire type. In that case, the articulated bending portion 30 is used instead of a guide wire for guiding the direction in which the catheter proceeds. Specifically, the catheter is connected to the non-inflating tube 3 without going through the articulated bending portion 30, and the articulated bending portion 30 (the end opposite to the mounting portion) is connected to the other end of the catheter, that is, on the opposite side of the non-inflating tube 3. Gas to be contained in the elastic tube 1 within the articulated bending portion 30 is injected from the non-inflating tube 3 through the catheter. Consequently, through adjustment of the pressure of the gas contained in the elastic tube body 11, the articulated bending portion 30 can guide the direction in which the catheter proceeds.

When a laser scalpel as a medical device is attached to the mounting portion, a cord that sends signals for controlling laser emitted by the laser scalpel can double as the non-stretching body 4. The medical device to be attached to the elastic tube 1 may also be an electric scalpel.

(Other Representations of the Present Invention)

The present invention can also be represented as follows.

An endoscope device according to the present invention may be represented as an endoscope device that includes: an articulated bending device consisting of multiple inflatable elastic tubes each of which has a flexible non-stretching body fixed in the length direction in an elastic tube portion, has an elongated hollow cylindrical shape, and is sealed at a distal end portion and contains fluid therein; a camera mounted at the distal end portion of the articulated bending device; non-inflating tubes that are connected to and communicate with the other ends of the elastic tube portions and have a shape of a hollow cylinder in which fluid is contained; a hollow, cylindrical connecting tube connected with the non-inflating tube portion and having flexibility and non-inflatability; and a control unit that controls the fluid pressure in the elastic tubes through the connecting tube and the non-inflating tubes by varying the fluid pressure, in which the control unit controls the fluid pressure in the elastic tubes so that the fluid pressure inflates and deflates the elastic tubes on the opposite side of the non-stretching body, thereby making the articulated bending device curve at a certain angle.

The endoscope device according to the present invention is the endoscope device having the above-described configuration, in which the control unit may be configured to include a piston and a syringe for changing the fluid pressure in the elastic tubes; a fluid pressure sensor for detecting the fluid pressure; a piston driving unit for actuating the piston in the syringe to vary the fluid pressure; a microphone for inputting voice of the operator; and a pressurization control unit to which voice signals input through the microphone and detection signals from the fluid pressure sensor are input and which controls the piston driving unit, and the pressurization control unit may control the piston driving unit based on the voice of the operator to change the fluid pressure in the elastic tubes.

The endoscope device according to the present invention is the endoscope device having the above-described configuration, in which the non-stretching body may be fabricated from polyamide fiber.

The endoscope device according to the present invention is the endoscope device having the above-described configuration, in which the non-stretching body may be an electric cord for supplying electric power to the camera.

[Summarization]

A bending device (articulated bending portion 30) according to the first aspect of the present invention includes: a tubular member (elastic tube 1P) having a hollow structure; and a plurality of elastic tubes (1*a* to 1*d*) disposed inside the tubular member, in which the elastic tubes each include an elastic tube body (11) which is sealed at a distal end portion thereof and has an elongated hollow cylindrical shape, and a non-stretching body (4) for suppressing inflation of the elastic tube body, the non-stretching body is fixed to the elastic tube body, a portion of the elastic tube body in which the non-stretching body is fixed is thicker than a remaining portion of the elastic tube body, the tubular member has a multi-layer structure (outer peripheral elastic tubes 1*k*, 1*m*, and 1*n*) on a shape of a cross section orthogonal to an axis direction of the tubular member, and a portion of the elastic tube body opposite the portion in which the non-stretching body is fixed inflates in a circumferential direction of the elastic tube body in response to increase in an internal pressure of the elastic tube body and the tubular member bends in a step-wise angle corresponding to a number of layers of the multi-layer structure.

With this configuration, since the elastic tube has the non-stretching body, the thick wall portion of the elastic tube body in a part opposite the position where the non-stretching body is disposed inflates in the circumferential direction of the elastic tube body in response to increase in the internal pressure. Thus, bending of the tubular member relative to the amount of inflation is large when compared to a case of uniform inflation of the elastic tube body in the entire circumferential direction. This permits the tubular member to be easily bent without applying large pressure to the elastic tube body.

Further, with the configuration above, the tubular member bends in a step-wise angle in accordance with the number of layers of the multi-layer structure. Accordingly, a curving angle desired by an operator can be realized with higher accuracy than the case where an outer peripheral elastic tube singularly constitutes the tubular member.

Further, with the configuration above, since the portion of the elastic tube body in which the non-stretching body is fixed is thicker than the remaining portion, the portion in which the non-stretching body is fixed has improved durability and also has increased non-stretchability, leading to such an effect of enabling stable bending motions with no hysteresis generated to pressurization.

In the bending device according to the second aspect of the present invention, the tubular member may have a gap in the multi-layer structure in the first aspect.

With this configuration, even if an inner most circumferential member constituting the multi-layer structure starts inflation thereof in response to inflation of the elastic tube body, the members of the second and following layers do not immediately inflate due to the presence of the gap. Accordingly, further step-wise suppression of inflation of the tubular member can be achieved.

In the bending device according to the third aspect of the present invention, the multi-layer structure may be composed of a plurality of outer peripheral elastic tubes forming a nested structure in the first or second aspect.

With this configuration, the multi-layer structure in the tubular member is composed of a plurality of outer peripheral elastic tubes. Accordingly, variation in bending motion characteristics of the tubular member, which is caused by the change of the elastic modulus, the wall thickness, and the like of the outer peripheral elastic tubes, is smaller than the case where a single outer peripheral elastic tube constitutes the tubular member. Consequently, variation in curving angles depending on bending portions is reduced. Further, compared to the case of a single outer peripheral elastic tube, inflation in the elastic tube circumferential direction (the lateral direction), which does not contribute to bending, can be further suppressed and bending caused by inflation in the long-axis direction (the vertical direction), which directly affects the control of the curving angle, can be further effectively created. Further, since unnecessary inflation in the elastic tube circumferential direction is further suppressed, degradation of the elastic tubes caused by mechanical stress that occurs from repeated inflations and deflations can be more effectively prevented as well.

Further, with the configuration above, since the tubular member bends in a step-wise angle in accordance with the number of outer peripheral elastic tubes, a curving angle desired by an operator can be realized with higher accuracy.

In the bending device according to the fourth aspect of the present invention, the plurality of outer peripheral elastic tubes may have different elastic modules from each other in the third aspect.

With this configuration, a user such as an operator can arbitrarily vary the elastic modulus of each outer peripheral elastic tube. Here, as the bending motion characteristics of the bending device are influenced by the elastic modulus of the outer peripheral elastic tube, the bending device having the bending motion characteristics desired by a user can be realized.

In the bending device according to the fifth aspect of the present invention, the tubular member may be composed of the outer peripheral elastic tube and elastic tubes (1*m* and 1*n*) which are disposed inside the outer peripheral elastic tube and whose cross section in a circumferential direction has a wave shape in the first or second aspect.

With this configuration, the elastic tube whose cross section in the circumferential direction has a wave shape is disposed inside the outer peripheral elastic tube in the tubular member. Therefore, tension is hardly applied until the outer circumferential surface of the elastic tube having the wave shape becomes to be flat in response to inflation. Accordingly, an advantageous effect equivalent to that in the case providing a gap among the outer peripheral elastic tubes can be obtained and the outer diameter of the bending device can be reduced due to the reduction in a region for the gap portion.

In the bending device according to the sixth aspect of the present invention, the tubular member may be composed of an outer peripheral elastic tube and an anisotropically-stretchable elastic body which is disposed inside the outer peripheral elastic tube and has a tubular shape in the first or second aspect.

With this configuration, an anisotropically-stretchable elastic body having a tubular shape is disposed inside the outer peripheral elastic tube in the tubular member. Here, the anisotropically-stretchable elastic body has directionality in the stretch characteristics thereof. Therefore, inflation in the elastic tube circumferential direction (the lateral direction), which does not contribute to bending, can be further suppressed and bending caused by inflation in the long-axis direction (the vertical direction), which directly affects the control of the curving angle, can be further effectively created.

Further, with the configuration above, variation in curving angles depending on bending portions can be largely improved.

In the bending device according to the seventh aspect of the present invention, the anisotropically-stretchable elastic body may be an elastic tube (elastic tube body 11) having a bellows structure in the sixth aspect.

In the bending device according to the eighth aspect of the present invention, the anisotropically-stretchable elastic body may be a mesh-like elastic body (12) in the sixth aspect.

With this configuration, a bending device having a smaller diameter, higher bendability, and smaller variation in curving angles depending on bending portions can be realized.

In the bending device according to the ninth aspect of the present invention, anisotropically-stretchable elastic bodies having a tubular shape may be respectively provided around the plurality of elastic tubes in any one of the first to eighth aspects.

With this configuration, since the elastic tube body has the non-stretching body, the thick wall portion of the elastic tube body in a part opposite the position where the non-stretching body is disposed inflates in the circumferential direction of the elastic tube body in response to increase in the internal pressure. Thus, bending of the tubular member relative to the amount of inflation is large when compared to a case of uniform inflation of the elastic tube body in the entire circumferential direction. This permits the tubular member to be easily bent without applying large pressure to the elastic tube body.

Further, with the configuration above, the elastic tubes have different stretch characteristics in the bending directions thereof. Therefore, inflation in the elastic tube circumferential direction (the lateral direction), which does not contribute to bending, can be further suppressed and bending caused by inflation in the long-axis direction (the vertical direction), which directly affects the control of the curving angle, can be further effectively created.

Further, with the configuration above, variation in curving angles depending on bending portions can be largely improved.

In the bending device according to the tenth aspect of the present invention, a plurality of anisotropically-stretchable elastic bodies having stretch characteristics different from each other may be provided between an inner circumferential surface and an outer circumferential surface of the plurality of elastic tubes in any one of the first to eighth aspects.

This configuration enables the elastic tubes themselves to have step-wise stretch characteristics. Further, since the elastic tube and the anisotropically-stretchable elastic bodies are integrated with each other, the diameter of the bending device can be further reduced and hysteresis characteristics of the elastic tube are lowered, being able to improve controllability of bending of the bending portion.

In the bending device according to the eleventh aspect of the present invention, the anisotropically-stretchable elastic body may be a mesh-like elastic body in the ninth or tenth aspect.

With this configuration, a bending device having a smaller diameter, higher bendability, and smaller variation in curving angles depending on bending portions can be realized.

A bending device (articulated bending portion 30) according to the twelfth aspect of the present invention includes: a tubular member having a hollow structure; and a plurality of elastic tubes disposed inside the tubular member, in which the elastic tubes each include an elastic tube body which is sealed at a distal end portion thereof and has an elongated hollow cylindrical shape, and a non-stretching body for suppressing inflation of the elastic tube body, the non-stretching body is provided along a thick wall portion of the elastic tube body, the elastic tubes have a multi-layer structure on a shape of a cross section orthogonal to an axis direction of the elastic tubes, and a portion of the elastic tube body opposite the thick wall portion in which the non-stretching body is disposed inflates in a circumferential direction of the elastic tube body in response to increase in an internal pressure of the elastic tube body and the tubular member bends in a step-wise angle.

With this configuration, since the elastic tube has the non-stretching body, the thick wall portion of the elastic tube body in a part opposite the position where the non-stretching body is disposed inflates in the circumferential direction of the elastic tube body in response to increase in the internal pressure. Thus, bending of the tubular member relative to the amount of inflation is large when compared to a case of uniform inflation of the elastic tube body in the entire circumferential direction. This permits the tubular member to be easily bent without applying large pressure to the elastic tube body.

Further, with the configuration above, the tubular member bends in a step-wise angle. Therefore, a curving angle desired by an operator can be realized with higher accuracy.

In the bending device according to the thirteenth aspect of the present invention, the multi-layer structure may be composed of the elastic tube body and an anisotropically-stretchable elastic body (mesh-like elastic bodies 12*a* and 12*b*) which is provided around the elastic tube body in the twelfth aspect.

With this configuration, the elastic tubes have different stretch characteristics in the bending direction thereof. Accordingly, interference by other elastic tubes with respect to a bending motion of a specific elastic tube can be reduced. Specifically, inflation in the elastic tube circumferential direction (the lateral direction), which does not contribute to bending, can be further suppressed and bending caused by inflation in the long-axis direction (the vertical direction), which directly affects the control of the curving angle, can be further effectively created.

Further, with the configuration above, variation in curving angles depending on bending portions can be largely improved.

Additionally, a moderate allowance with respect to inflation can be provided as well by using a gap in the layer structure without increasing the outer diameter of the outermost peripheral elastic tube. Therefore, the bending motion can be controlled with high accuracy. Further, the presence of the above-mentioned moderate allowance increases the freedom in design of the elastic tubes.

In the bending device according to the fourteenth aspect of the present invention, the multi-layer structure may be composed of the elastic tube body and an anisotropically-stretchable elastic body (mesh-like elastic bodies 12*a* and 12*b*) which is provided between an inner circumferential surface and an outer circumferential surface of the elastic tube body in the twelfth aspect.

This configuration enables the elastic tubes themselves to have step-wise stretch characteristics. Further, since the elastic tube and the anisotropically-stretchable elastic bodies are integrated with each other, the diameter of the bending device can be further reduced and hysteresis characteristics of the elastic tube are lowered, being able to improve controllability of bending of the bending portion.

In the bending device according to the fifteenth aspect of the present invention, the anisotropically-stretchable elastic body may be a mesh-like elastic body in the thirteenth or fourteenth aspect.

With this configuration, a bending device having a smaller diameter, higher bendability, and smaller variation in curving angles depending on bending portions can be realized.

A control device (20) according to the sixteenth aspect of the present invention is a control device for controlling inflation and deflation of the elastic tube body according to the first aspect or the twelfth aspect, and may be configured to include: an instruction receiving unit for receiving an instruction for inflating or deflating the elastic tubes; and a fluid pressure varying unit for changing a pressure by injecting fluid into a hollow interior of the elastic tube body based on the instruction received by the instruction receiving unit.

With this configuration, since a distal end portion of a medical instrument is manipulated by the control device, a camera assistant for manipulating the distal end portion is not required and a medical procedure conducted by an operator would not be interfered by a motion and the like of the camera assistant. Accordingly, the operator can conduct the medical procedure smoothly.

A medical instrument (an endoscope device 100) according to the seventeenth aspect of the present invention may be configured to include the bending device according to the first or twelfth aspect and the control device according to the sixteenth aspect.

With this configuration, by using the bending device at a distal end portion of the medical instrument, for example, the medial instrument which has a simple structure but is capable of producing an elaborate bending motion exhibiting high degree of freedom of the bending device with excellent controllability can be realized.

The present invention is not limited to the embodiments described above but permits various modifications within the scope defined by claims. An embodiment made by combining technical means disclosed in different embodiments appropriately is encompassed in the technical scope of the present invention. Moreover, a novel technical feature can be formed by combining technical means disclosed in different embodiments.

INDUSTRIAL APPLICABILITY

The present invention can be suitably applied to articulated bending devices, control devices, and medical instruments. The present invention is applicable to medical instruments equipped with endoscope cameras, catheters, laser scalpels, and electric scalpels in medical settings in particular.

REFERENCE SIGNS LIST

1 elastic tube
1*a* to 1*h* elastic tube
1*j*, 1*k*, 1*m*, 1*n* elastic tube
2 endoscope camera
3 non-inflating tube
4 non-stretching body
5 connecting tube
10 endoscope part (medical instrument part)
11 elastic tube body
12 mesh sheet (mesh-like elastic body)
13 fixing portion
20 control device
21 piston (air pressure varying unit)
22 syringe
23 air pressure sensor
24 piston driving unit (air pressure varying unit)
25 microphone (instruction receiving unit)
26 pressurization control unit (air pressure varying unit)
30 articulated bending portion (bending device)
31 bending portion (joint)
32 non-bending portion
33 rigid tube
34 non-inflating body
35 pressurizing portion
36 pressurizing valve
100 endoscope device (medical instrument)

The invention claimed is:

1. A bending device comprising:

a tubular member having a hollow structure; and a plurality of elastic tubes disposed inside the tubular member, wherein the elastic tubes each include an elastic tube body which is sealed at a distal end portion thereof and has an elongated hollow cylindrical shape, and a non-stretching body to suppress inflation of the elastic tube body, the non-stretching body is fixed to the elastic tube body and at least partially located within an interior portion of the elastic tube body, a portion of the elastic tube body in which the non-stretching body is fixed is thicker than a remaining portion of the elastic tube body, the tubular member has a multi-layer structure in a cross section of the tubular member that is orthogonal to an axis direction of the tubular member, a portion of the elastic tube body opposite the portion in which the non-stretching body is fixed inflates in a circumferential direction of the elastic tube body in response to an increase in an internal pressure of the elastic tube body and the tubular member bends in a step-wise angle corresponding to a number of layers of the multi-layer structure, and in each of the elastic tubes, the non-stretching body is provided on an inner side of each of the elastic tubes, which is a side closest to a central longitudinal axis of the tubular member.

2. The bending device according to claim 1, wherein the tubular member has a gap in the multi-layer structure.

3. The bending device according to claim 1, wherein the multi-layer structure is composed of a plurality of outer peripheral elastic tubes forming a nested structure.

4. The bending device according to claim 3, wherein the plurality of outer peripheral elastic tubes have different elastic moduluses from each other.

5. The bending device according to claim 1, wherein the multi-layer structure is composed of an outer peripheral elastic tube and an elastic tube which is disposed inside the outer peripheral elastic tube and whose cross section in a circumferential direction has a wave shape.

6. The bending device according to claim 1, wherein the multi-layer structure is composed of an outer peripheral elastic tube and an anisotropically-stretchable elastic body which is disposed inside the outer peripheral elastic tube and has a tubular shape.

7. The bending device according to claim 6, wherein the anisotropically-stretchable elastic body is an elastic tube having a bellows structure.

8. The bending device according to claim 6, wherein the anisotropically-stretchable elastic body is a mesh-like elastic body.

9. The bending device according to claim 1, wherein anisotropically-stretchable elastic bodies having a tubular shape are respectively provided around the plurality of elastic tubes.

10. The bending device according to claim 9, wherein the anisotropically-stretchable elastic body is a mesh-like elastic body.

11. The bending device according to claim 1, wherein a plurality of an isotropically-stretchable elastic bodies having stretch characteristics different from each other are provided between an inner circumferential surface and an outer circumferential surface of the plurality of elastic tubes.

12. A bending device comprising:

a tubular member having a hollow structure; and a plurality of elastic tubes disposed inside the tubular member, wherein the elastic tubes each include an elastic tube body which is sealed at a distal end portion thereof and has an elongated hollow cylindrical shape, and a non-stretching body to suppress inflation of the elastic tube body, the non-stretching body is provided along a thick wall portion of the elastic tube body, the elastic tubes have a multi-layer structure in a cross section of the tubular member that is orthogonal to an axis direction of the elastic tubes, a portion of the elastic tube body opposite the thick wall portion in which the non-stretching body is disposed inflates in a circumferential direction of the elastic tube body in response to an increase in an internal pressure of the elastic tube body and the tubular member bends in a step-wise angle, and in each of the elastic tubes, the non-stretching body is provided on an inner side of each of the elastic tubes, which is a side closest to a central longitudinal axis of the tubular member.

13. The bending device according to claim 12, wherein the multi-layer structure is composed of the elastic tube body and an anisotropically-stretchable elastic body which is provided around the elastic tube body.

14. The bending device according to claim 13, wherein the anisotropically-stretchable elastic body is a mesh-like elastic body.

15. The bending device according to claim 12, wherein the multi-layer structure is composed of the elastic tube body and an anisotropically-stretchable elastic body which is provided between an inner circumferential surface and an outer circumferential surface of the elastic tube body.

16. A control device for controlling inflation and deflation of the elastic tube body according to claim 1, the control device comprising:

a microphone that receives an instruction for inflating or deflating the elastic tubes; and a piston that changes a pressure by injecting fluid into a hollow interior of the elastic tube body based on the instruction received by the instruction receiving unit.

17. A medical instrument comprising:

the bending device according to claim 1; and a controller that controls inflation and deflation of the elastic tube body, the controller including:

an instruction receiver that receives an instruction to inflate or deflate the elastic tubes; and a fluid pressure controller that changes a pressure by injecting fluid into a hollow interior of the elastic tube body based on the instruction received by the instruction receiver.

* * * * *